United States Patent [19]

Nefzi et al.

[11] Patent Number: 5,786,448
[45] Date of Patent: Jul. 28, 1998

[54] COMBINATORIAL LIBRARIES OF CYCLIC UREA AND CYCLIC THIOUREA DERIVATIVES AND COMPOUNDS THEREIN

[75] Inventors: Adel Nefzi, San Diego; John M. Ostresh, Encinitas; Richard Houghten, Del Mar, all of Calif.

[73] Assignee: Trega Biosciences, Inc., San Diego, Calif.

[21] Appl. No.: 745,793

[22] Filed: Nov. 7, 1996

[51] Int. Cl.$^6$ ............ A61K 38/12; C07D 233/38
[52] U.S. Cl. ............ 530/317; 530/331; 530/334; 548/316.4; 548/317.1; 544/242
[58] Field of Search ............... 530/317, 331, 530/334; 548/316.4, 317.1; 544/242

[56] References Cited

U.S. PATENT DOCUMENTS

| | | | |
|---|---|---|---|
| 4,795,815 | 1/1989 | Ternansky | 548/112 |
| 4,940,718 | 7/1990 | Barnett et al. | 514/370 |
| 5,182,366 | 1/1993 | Huebner et al. | 530/334 |

OTHER PUBLICATIONS

Singh et al., Indian J. Chem. vol. 14 B Jul. 1976 pp. 528–531.

Cuervo et al., "Polyalkylamine chemical combinatorial libraries." *Peptides*, 465–466 (1995).

Dorner et al., "The synthesis of peptidomimetic combinatorial libraries through successive amide alkylations." *Bioorg. & Med. Chem.*, 4(5):709–715 (1996).

Gallop et al., "Applications of combinatorial technologies to drug discovery. 1. Background and peptide combinatorial libraries." *J. of Med. Chem.*, 37(9):1233–1251 (1994).

Gordon et al., "Application of combinatorial technologies to drug discovery. 2. Combinatorial organic synthesis, library screening strategies, and future directions." *J. of Med. Chem.*, 37 (10):1386–1401 (1994).

Houghten et al., "Generation and use of synthetic peptide combinatorial libraries for basic research and drug discovery." *Nature*, 354:84–86 (1991).

Kim et al., "Synthesis of a cyclic urea as a nonnatural biopolymer scaffold." *Tetrahedron Lett.*, 37:5309–5312 (1996).

Lam et al., "Rational design of potent, bioavailable, nonpeptide cyclic ureas as HIV protease inhibitors." *Science*, 263:380–384 (1994).

Ostresh et al., "Libraries from libraries: Chemical transformation of combinatorial libraries to extend the range and repertoire of chemical diversity." *Proc. Natl. Acad. Sci.*, 91:11138–11142 (1994).

Ostresh et al., "Generation and use of nonsupport-bound peptide and peptidomimetic combinatorial libraries." *Combinatorial Chemistry*, 267:220–234 (1996).

Pinilla et al., "Rapid identification of high affinity peptide ligands using positional scanning synthetic peptide combinatorial libraries." *Biotechniques*, 13:901–905 (1992).

Pinilla et al., "Versatility of positional scanning synthetic combinatorial libraries for the identification of individual compounds." *Drug Dev. Res.*, 33:133–145 (1994).

CA '86: 29756 N to Singh et al.

*Primary Examiner*—Cecilia J. Tsang
*Assistant Examiner*—Bennett Celsa
*Attorney, Agent, or Firm*—Campbell & Flores LLP

[57] ABSTRACT

The invention provides a rapid approach for combinatorial synthesis and screening of libraries of cyclic urea and cyclic thiourea compounds. The present invention further provides the compounds made by the combinatorial synthesis.

49 Claims, 10 Drawing Sheets

COMBINATORIAL LIBRARIES OF CYCLIC UREA AND CYCLIC THIOUREA DERIVATIVES AND COMPOUNDS THEREIN

BACKGROUND OF THE INVENTION

1. Field of the Invention

The present invention relates generally to the combinatorial synthesis of urea derivatives. More specifically, the invention provides novel cyclic ureas and thioureas as well as novel combinatorial libraries comprised of many such compounds, and methods of synthesizing the libraries.

2. Background Information

The process of discovering new therapeutically active compounds for a given indication involves the screening of all compounds from available compound collections. From the compounds tested one or more structure(s) is selected as a promising lead. A large number of related analogs are then synthesized in order to develop a structure-activity relationship and select one or more optimal compounds. With traditional one-at-a-time synthesis and biological testing of analogs, this optimization process is long and labor intensive. Adding significant numbers of new structures to the compound collections used in the initial screening step of the discovery and optimization process cannot be accomplished with traditional one-at-a-time synthesis methods, except over a time frame of months or even years. Faster methods are needed that allow for the preparation of up to thousands of related compounds in a matter of days or a few weeks. This need is particularly evident when it comes to synthesizing more complex compounds, such as the cyclic urea and thiourea compounds of the present invention.

Solid-phase techniques for the synthesis of peptides have been extensively developed and combinatorial libraries of peptides have been generated with great success. During the past four years there has been substantial development of chemically synthesized combinatorial libraries (SCLs) made up of peptides. The preparation and use of synthetic peptide combinatorial libraries has been described, for example, by Dooley in U.S. Pat. No. 5,367,053, Huebner in U.S. Pat. No. 5,182,366, Appel et al. in WO PCT 92/09300, Geysen in published European Patent Application 0 138 855 and Pirrung in U.S. Pat. No. 5,143,854. Such SCLs provide the efficient synthesis of an extraordinary number of various peptides in such libraries and the rapid screening of the library which identifies lead pharmaceutical peptides.

Peptides have been, and remain, attractive targets for drug discovery. Their high affinities and specificities toward biological receptors as well as the ease with which large peptide libraries can be combinatorially synthesized make them attractive drug targets. The screening of peptide libraries has led to the identification of many biologically-active lead compounds. However, the therapeutic application of peptides is limited by their poor stability and bioavailability in vivo. Therefore, there is a need to synthesize and screen compounds which can maintain high affinity and specificity toward biological receptors but which have improved pharmacological properties relative to peptides.

Combinatorial approaches have recently been extended to "organic," or non-peptide, libraries. The organic libraries to the present, however, are of limited diversity and generally relate to peptidomimetic compounds; in other words, organic molecules that retain peptide chain pharmacophore groups similar to those present in the corresponding peptide. Although the present invention is principally derived from the synthesis of dipeptides, the dipeptides are substantially modified. In short, they are chemically modified through alkylation, acylation, reduction, and cyclization into the subject ureas, thus providing mixtures and individual compounds of substantial diversity.

Significantly, many biologically active compounds contain cyclic ureas. Cyclic ureas have been reported by Lam et al., *Science*, 263:380 (1994), to be useful as inhibitors of human immunodeficiency virus (HIV) protease and HIV replication. Recently, Kim et al., *Tetrahedron Lett.*, 37:5309 (1996), illustrated the synthesis of oligomeric cyclic ureas as a non-natural biopolymer. Because cyclic urea moieties are found in many biologically active compounds and are known to have useful therapeutic implications, there is a need to further study and develop large numbers of cyclic ureas and their binding to biological receptors.

This invention satisfies these needs and provides related advantages as well. The present invention overcomes the known limitations to classical organic synthesis of cyclic ureas as well as the shortcomings of combinatorial chemistry with small organics or peptidomimetics. Moreover, the present invention provides a large array of diverse cyclic ureas which can be screened for biological activity, and as described below, are biologically active.

SUMMARY OF THE INVENTION

The invention provides a rapid approach for combinatorial synthesis and screening of libraries of cyclic urea and cyclic thiourea compounds. The present invention further provides the compounds made by the combinatorial synthesis. More specifically, the present invention relates to the generation of synthetic combinatorial libraries of organic compounds based on the formula:

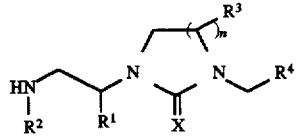

wherein $R^1$, $R^2$, $R^3$, $R^4$, X and n have the meanings provided below.

BRIEF DESCRIPTION OF THE DRAWINGS

FIG. 2 provides the RP-HPLC and LCQ-Mass spectra data for two individual compounds within the subject libraries, one cyclic urea (X=O.

DETAILED DESCRIPTION OF THE INVENTION

Figure 1:
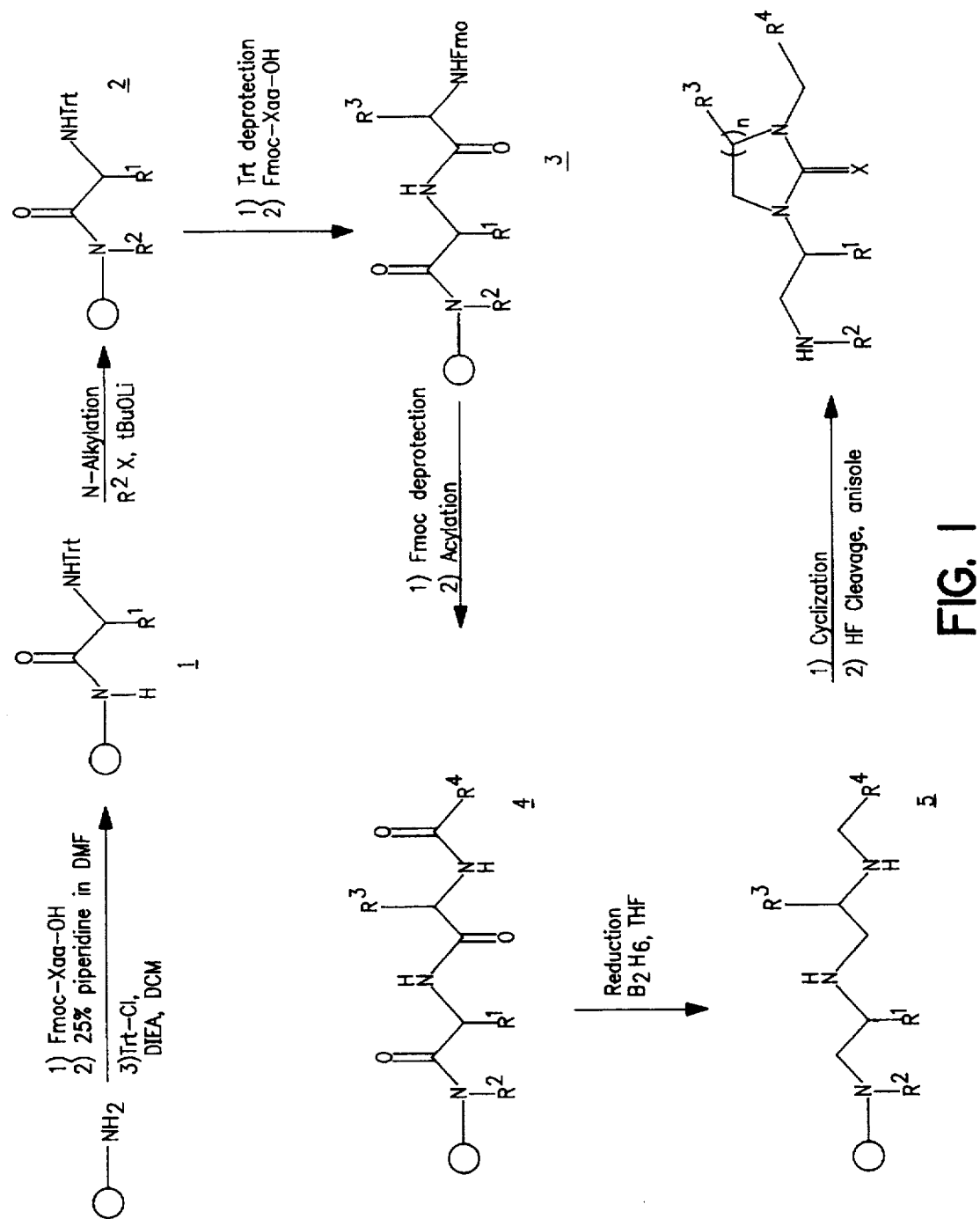
FIG. 1 shows the Reaction Scheme I for preparing libraries and compounds of the present invention.
Figure 2A:
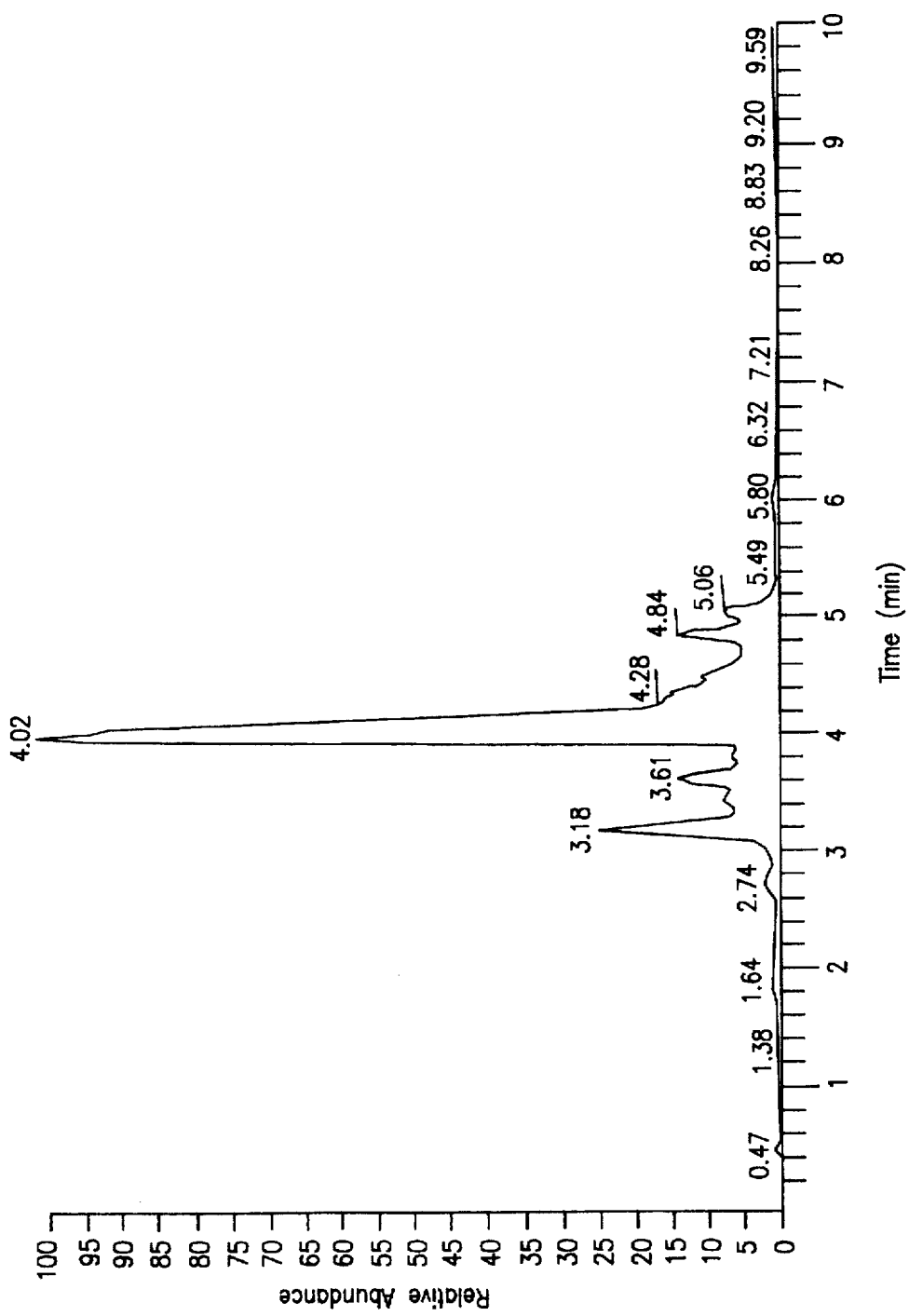
FIG. 2a and 2b) and one cyclic thiourea (X=S.
Figure 2B:
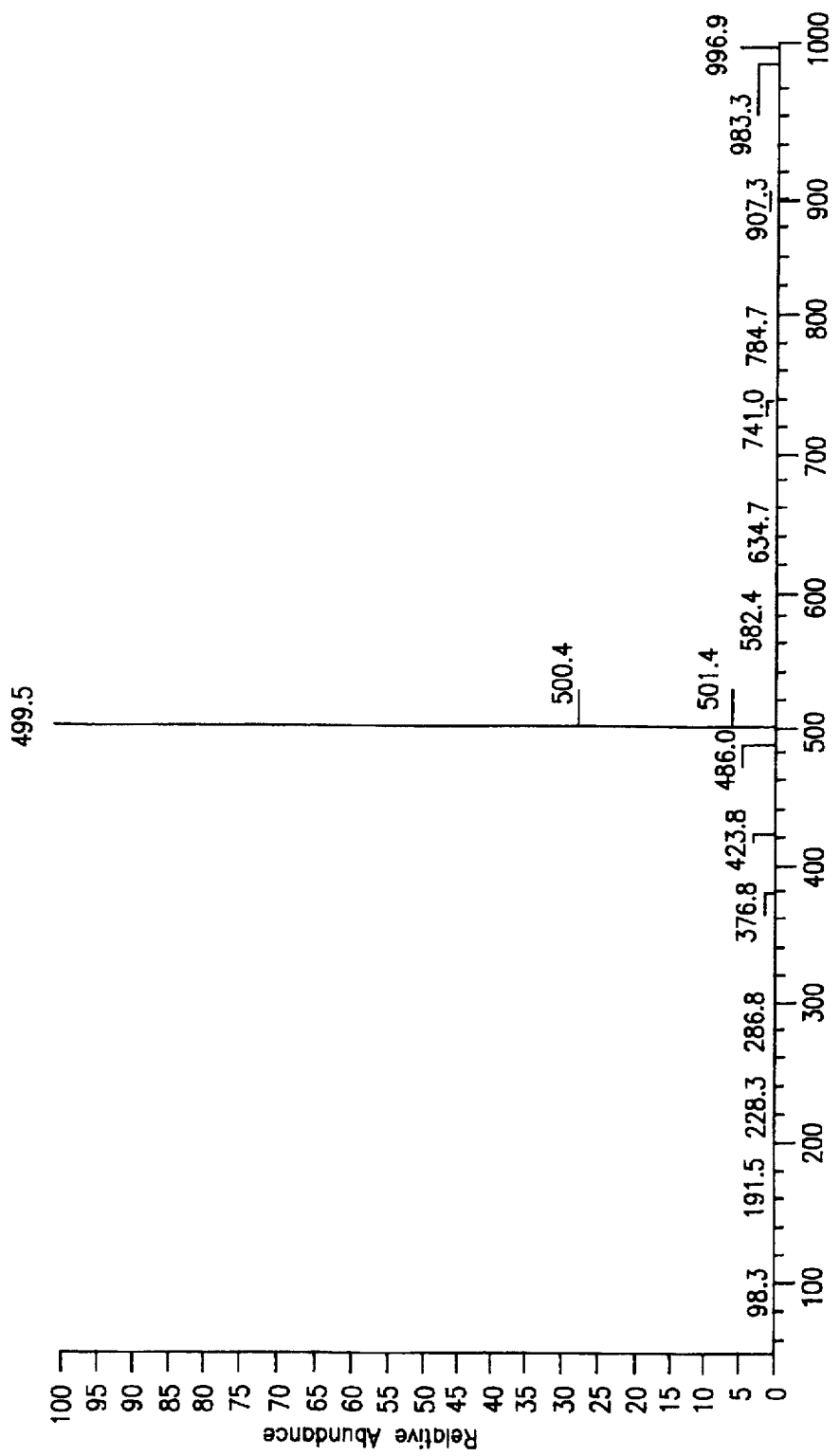
Figure 2C:
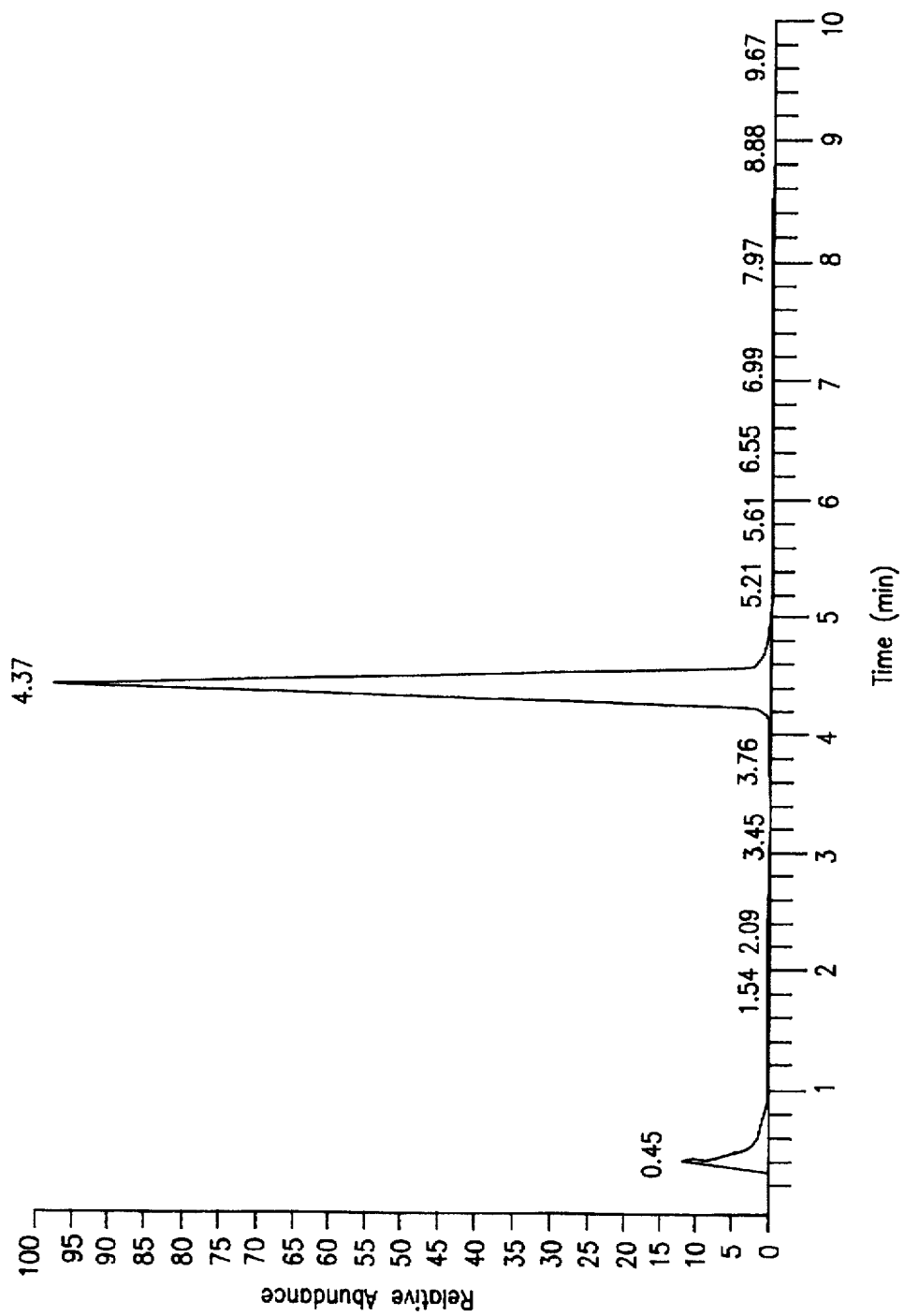
FIG. 2c and 2d).
Figure 2D:
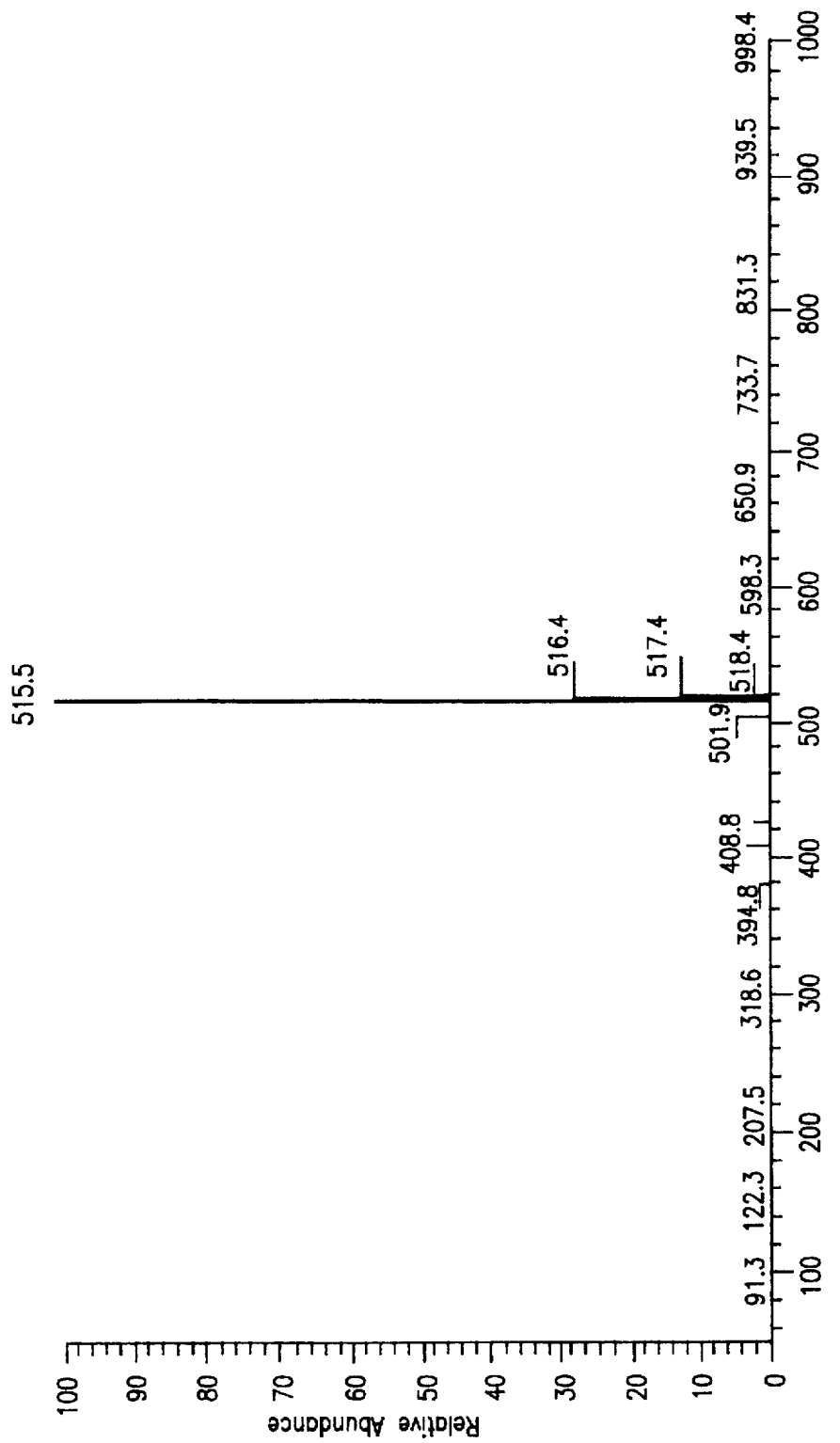

The present invention relates to the generation of synthetic combinatorial libraries and individual compounds which are based on the Formula I:

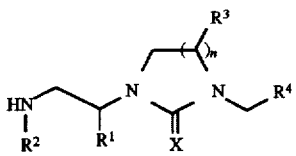

FORMULA I

In the above Formula I:

R$^1$ is a hydrogen atom, C$_1$ to C$_{10}$ alkyl; C$_1$ to C$_{10}$ substituted alkyl, C$_7$ to C$_{16}$ phenylalkyl, C$_7$ to C$_{16}$ substituted phenylalkyl, phenyl, substituted phenyl, C$_3$ to C$_7$ cycloalkyl, or C$_3$ to C$_7$ substituted cycloalkyl;

R$^2$ is C$_1$ to C$_{10}$ alkyl, C$_2$ to C$_{10}$ alkenyl, benzyl, substituted benzyl, naphthyl, or substituted naphthyl and, preferably, is methyl, ethyl, benzyl, allyl, or naphtylmethyl, more preferably 2-naphthylmethyl, and R$^2$ is most preferably methyl or benzyl;

R$^3$ is a hydrogen atom, C$_1$ to C$_{10}$ alkyl; C$_1$ to C$_{10}$ substituted alkyl, C$_7$ to C$_{16}$ phenylalkyl, C$_7$ to C$_{16}$ substituted phenylalkyl, phenyl, substituted phenyl, C$_3$ to C$_7$ cycloalkyl, or C$_3$ to C$_7$ substituted cycloalkyl;

R$^4$ is C$_1$ to C$_{10}$ alkyl, C$_2$ to C$_{10}$ alkenyl, C$_1$ to C$_{10}$ substituted alkyl, C$_3$ to C$_7$ substituted cycloalkyl, C$_7$ to C$_{16}$ phenylalkyl, C$_7$ to C$_{16}$ substituted phenylalkyl, C$_7$ to C$_{16}$ phenylalkenyl or C$_7$ to C$_{16}$ substituted phenylalkenyl;

X is an oxygen atom(O) or a sulfur atom(S); and n is one or two.

In one embodiment of the above cyclic ureas and thiourea libraries and compounds, the substituents are as follows:

R$^1$ is methyl, benzyl, hydrogen, 2-butyl, N,N-dimethylaminobutyl, N-methylaminobutyl, 2-methylpropyl, methylsulfinylethyl, N,N-dimethylaminoethyl, N,N-dimethylaminopropyl, N',N', N' -trimethylguanidinopropyl, hydroxymethyl, 1-hydroxyethyl, 2-propyl, N-methyl-3-indolylmethyl, 4-methoxybenzyl, 4-hydroxybenzyl, propyl, butyl, cyclohexylmethyl, phenyl, 2-naphthylmethyl, or 4-imidazolylmethyl;

R$^2$ is methyl;

R$^3$ is methyl, benzyl, hydrogen, 3-hydroxypropyl, 2-butyl, N-methylaminobutyl, aminobutyl, 2-methylpropyl, methylsulfinylethyl, guanidinopropyl, hydroxymethyl, 1-hydroxyethyl, 2-propyl, N-methyl-3-indolylmethyl, 4-methoxybenzyl, 4-hydroxybenzyl, propyl, butyl, cyclohexylmethyl, phenyl, 2-naphthylmethyl, or 4-imidazolylmethyl;

R$^4$ is 1-phenyl-1-cyclopropylmethyl, 2-phenylbutyl, 3-phenylbutyl, m-tolylethyl, 3-fluorophenethyl, 3-bromophenethyl, (α,α,α-trifluoro-m-tolyl)ethyl, p-tolylethyl, 4-fluorophenethyl, 3-methoxyphenethyl, 4-bromophenethyl, 4-methoxyphenethyl, 4-ethoxyphenethyl, 4-isobutyl-α-methylphenethyl, 3,4-dichlorophenethyl, 3,5-bis(trifluoromethyl) phenethyl, 3-(3,4-dimethoxyphenyl)propyl, 4-biphenethyl, 3-phenyl-2-methyl-2-propenyl, 3-(2-trifluoromethylphenyl)-2-propenyl, 3,4-dimethoxyphenethyl, 3,4-(dihydroxy)phenylethyl, 3-(2-methoxyphenyl)-2-propenyl, benzyl, 3-(4-chlorophenyl)-2-propenyl, trans-phenyl-2-propenyl, m-xylyl, phenethyl, 3-phenylpropyl, 4-phenylbutyl, 3,5-bis(trifluoromethyl)benzyl, butyl, heptyl, isobutyryl, (+/−)-2-methylbutyl, isovaleryl, 3-methylvaleryl, 4-methylvaleryl, 2-butenyl, 3-butenyl, p-xylyl, neopentyl, tert-butylethyl, cyclohexylmethyl, cyclohexylethyl, cyclohexylbutyl, cycloheptylmethyl, ethyl, 2-methyl-1-cyclopropylmethyl, cyclobutylmethyl, cyclopentylmethyl, 3-cyclopentylpropyl, cyclohexanepropyl, 4-methyl-1-cyclohexylmethyl, 4-tert-butyl-1-cyclohexylmethyl, 4-methylcyclohexylethyl, 2-methyl-2-butenyl, 1-adamantylethyl, 2-(α,α,α-trifluoro-m-toluidino)-3-pyridylmethyl, 4-nitrophenethyl, 4-(nitrophenyl)butyl, 3-(4-nitrophenyl)-2-propenyl, 2-nitrobenzyl, 2,4-dinitrophenethyl, 4-biphenethyl, 2-chloro-5-nitrobenzyl, (4-pyridylthio)ethyl, 3,3-diphenylpropyl, 2-chloro-4-nitrobenzyl, 4-dimethylaminobenzyl, 4-nitrobenzyl, 3-dimethylaminobenzyl, abietyl, 2-methyl-4-nitro-1-imidizolylpropyl, trans-styrylethyl, cyclopentylethyl, 2,2-dicyclohexylethyl, (2-pyridylthio)ethyl, pentadienyl, or 3-indolylethyl;

X is an oxygen atom(O) or a sulfur atom(S); and n is one or two.

In one of the preferred embodiments of the present invention, the R groups are those as immediately defined above, when X is an oxygen atom. In yet another preferred embodiment, the R groups are those as immediately defined above and X is a sulfur atom.

In yet further embodiments of the subject cyclic ureas and thiourea libraries and compounds, the substituents are as follows:

R$^1$ is methyl, benzyl, hydrogen, 2-butyl, N-methyl-N-benzylaminobutyl, N-benzylaminobutyl, 2-methylpropyl, methylsulfinylethyl, N,N-dibenzylaminoethyl, N,N-dibenzylaminopropyl, guanidinopropyl, hydroxymethyl, 1-hydroxyethyl, 2-propyl, N-benzyl-3-indolylmethyl, 4-hydroxybenzyl, propyl, butyl, cyclohexylmethyl, phenyl, 2-naphthylmethyl, or 4-imidazolylmethyl;

R$^2$ is benzyl;

R$^3$ is methyl, benzyl, hydrogen, 3-hydroxypropyl, 2-butyl, N-methylaminobutyl, aminobutyl, 2-methylpropyl, methylsulfinylethyl, guanidinopropyl, hydroxymethyl, 1-hydroxyethyl, 2-propyl, N-methyl-3-indolylmethyl, 4-methoxybenzyl, 4-hydroxybenzyl, propyl, butyl, cyclohexylmethyl, phenyl, 2-naphthylmethyl, or 4-imidazolylmethyl;

R$^4$ is 1-phenyl-1-cyclopropylmethyl, 2-phenylbutyl, 3-phenylbutyl, m-tolylethyl, 3-fluorophenethyl, 3-bromophenethyl, (α,α,α-trifluoro-m-tolyl)ethyl, p-tolylethyl, 4-fluorophenethyl, 3-methoxyphenethyl, 4-bromophenethyl, 4-methoxyphenethyl, 4-ethoxyphenethyl, 4-isobutyl-α-methylphenethyl, 3,4-dichlorophenethyl, 3,5-bis(trifluoromethyl) phenethyl, 3-(3,4-dimethoxyphenyl) propyl, 4-biphenethyl, 3-phenyl-2-methyl-2-propenyl, 3-(2-trifluoromethylphenyl)-2-propenyl, 3,4-dimethoxyphenethyl, 3,4-(dihydroxy)phenylethyl, 3-(2-methoxyphenyl)-2-propenyl, benzyl, 3-(4-chlorophenyl)-2-propenyl, trans-phenyl-2-propenyl, m-xylyl, phenethyl, 3-phenylpropyl, 4-phenylbutyl, 3,5-bis(trifluoromethyl)benzyl, butyl, heptyl, isobutyryl, (+/−)-2-methylbutyl, isovaleryl, 3-methylvaleryl, 4-methylvaleryl, 2-butenyl, 3-butenyl, p-xylyl, neopentyl, tert-butylethyl, cyclohexylmethyl, cyclohexylethyl, cyclohexylbutyl, cycloheptylmethyl, ethyl, 2-methyl-1-cyclopropylmethyl, cyclobutylmethyl, cyclopentylmethyl, 3-cyclopentylpropyl, cyclohexanepropyl, 4-methyl-1-cyclohexylmethyl, 4-tert-butyl-1-cyclohexylmethyl, 4-methylcyclohexylethyl, 2-methyl-2-butenyl, 1-adamantylethyl, 2-(α,α,α-trifluoro-m-toluidino)-3-pyridylmethyl, 4-nitrophenethyl, 4-(nitrophenyl)butyl, 3-(4-nitrophenyl)-2-propenyl, 2-nitrobenzyl, 2,4-dinitrophenethyl, 4-biphenethyl, 2-chloro-5-nitrobenzyl, (4-pyridylthio)ethyl, 3,3-diphenylpropyl, 2-chloro-4-nitrobenzyl, 4-dimethylaminobenzyl, 4-nitrobenzyl, 3-dimethylaminobenzyl, abietyl, 2-methyl-4-nitro-1-imidizolylpropyl, trans-styrylethyl, cyclopentylethyl, 2,2-dicyclohexylethyl, (2-pyridylthio)ethyl, pentadienyl, or 3-indolylethyl;

X is an oxygen atom(O) or a sulfur atom(S); and n is one or two.

In one of the preferred embodiments of the present invention, the R groups are those as immediately defined above, when X is an oxygen atom. In yet another preferred embodiment, the R groups are those as immediately defined above and X is a sulfur atom.

In the above Formula the stereochemistry of the chiral $R^1$ through $R^4$ groups can independently be in the R or S configuration, or a mixture of the two. For instance, as will be described in further detail below the $R^1$ and $R^3$ groups are the side chains of the α-carbon of various amino acids. The amino acids can be in the L-or D-configuration, resulting in the same R group, varying only in its stereochemistry.

In the above Formulae, the term "$C_1$ to $C_{10}$ alkyl" denotes such radicals as methyl, ethyl, n-propyl, isopropyl, n-butyl, sec-butyl, tert-butyl, amyl, tert-amyl, hexyl, heptyl and the like. A preferred "$C_1$ to $C_{10}$ alkyl" group is methyl.

The term "$C_2$ to $C_{10}$ alkenyl" denotes such radicals as vinyl, allyl, 2-butenyl, 3-butenyl, 2-pentenyl, 3-pentenyl, 4-pentenyl, 2-hexenyl, 3-hexenyl, 4-hexenyl, 5-hexenyl, 2-heptenyl, 3-heptenyl, 4-heptenyl, 5-heptenyl, 6-heptenyl, as well as dienes and trienes of straight and branched chains.

The term "$C_2$ to $C_{10}$ alkynyl" denotes such radicals as ethynyl, propynyl, butynyl, pentynyl, hexynyl, heptynyl, as well as di- and tri-ynes.

The term "$C_1$ to $C_{10}$ substituted alkyl," "$C_2$ to $C_{10}$ substituted alkenyl," and "$C_2$ to $C_{10}$ substituted alkynyl," denotes that the above $C_1$ to $C_{10}$ alkyl groups and $C_2$ to $C_{10}$ alkenyl and alkynyl groups are substituted by one or more, and preferably one or two, halogen, hydroxy, protected hydroxy, $C_3$ to $C_7$ cycloalkyl, $C_3$ to $C_7$ substituted cycloalkyl, naphthyl, substituted naphthyl, adamantyl, abietyl, thiofuranyl, indolyl, substituted indolyl, amino, protected amino, (monosubstituted)amino, protected (monosubstituted)amino, (disubstituted)amino, guanidino, (monosubstituted)guanidino, (disubstituted)guanidino, (trisubstituted)guanidino, imidazolyl, pyrolidinyl, $C_1$ to $C_7$ acyloxy, nitro, heterocycle, substituted heterocycle, $C_1$ to $C_4$ alkyl ester, carboxy, protected carboxy, carbamoyl, carbamoyloxy, carboxamide, protected carboxamide, cyano, methylsulfonylamino, methylsulfonyl, sulfurhydryl, $C_1$ to $C_4$ alkylthio, $C_1$ to $C_4$ alkyl sulfonyl or $C_1$ to $C_4$ alkoxy groups. The substituted alkyl groups may be substituted once or more, and preferably once or twice, with the same or with different substituents.

Examples of the above substituted alkyl groups include the cyanomethyl, nitromethyl, chloromethyl, hydroxymethyl, tetrahydropyranyloxymethyl, trityloxymethyl, propionyloxymethyl, aminomethyl, I carboxymethyl, allyloxycarbonylmethyl, allylcaroxybonylaminomethyl, carbamoyloxymethyl, methoxymethyl, ethoxymethyl, t-butoxymethyl, acetoxymethyl, chloromethyl, bromomethyl, iodomethyl, 6-hydroxyhexyl, 2,4-dichloro(n-butyl), 2-amino(isopropyl), 2-carbamoyloxyethyl chloroethyl, bromoethyl, fluoroethyl, iodoethyl, chloropropyl, bromopropyl, fluoropropyl, iodopropyl and the like.

In preferred embodiments of the subject invention, $C_1$ to $C_{10}$ alkyl, $C_2$ to $C_{10}$ alkenyl, $C_2$ to $C_{10}$ alkynyl, $C_1$ to $C_{10}$ substituted alkyl, $C_2$ to $C_{10}$ substituted alkenyl, or $C_2$ to $C_{10}$ substituted alkynyl preferably $C_1$ to $C_7$, respectively, and more preferably, $C_1$ to $C_6$. However, it would be appreciated to those of skill in the art that one or a few carbons could be added to an alkyl, alkenyl, alkynyl, substituted or unsubstituted, without substantially modifying the structure and function of the subject compounds and that, therefore, such additions would not depart from the spirit of the invention.

The term "$C_1$ to $C_4$ alkoxy" as used herein denotes groups such as methoxy, ethoxy, n-propoxy, isopropoxy, n-butoxy, t-butoxy and like groups. A preferred $C_1$ to $C_4$ alkoxy group is methoxy.

The term "$C_1$ to $C_7$ acyloxy" denotes herein groups such as formyloxy, acetoxy, propanoyloxy, butanoyloxy, pentanoyloxy, hexanoyloxy, heptanoyloxy, and the like.

Similarly, the term "$C_1$ to $C_7$ acyl" encompasses groups such as formyl, acetyl, propionoyl, butyroyl, pentanoyl, hexanoyl, heptanoyl, benzoyl and the like.

The substituent term "$C_3$ to $C_7$ cycloalkyl" includes the cyclopropyl, cyclobutyl, cyclopentyl, cyclohexyl or cycloheptyl rings. The substituent term "$C_3$ to $C_7$ substituted cycloalkyl" indicates the above cycloalkyl rings substituted by a halogen, hydroxy, protected hydroxy, phenyl, substituted phenyl, heterocycle, substituted heterocycle, $C_1$ to $C_{10}$ alkyl, $C_1$ to $C_4$ alkoxy, carboxy, protected carboxy, amino, or protected amino.

The substituent term "$C_3$ to $C_7$ cycloalkenyl" indicates a 1,2, or 3-cyclopentenyl ring, a 1,2,3 or 4-cyclohexenyl ring or a 1,2,3,4 or 5-cycloheptenyl ring, while the term "substituted $C_3$ to $C_7$ cycloalkenyl" denotes the above $C_3$ to $C_7$ cycloalkenyl rings substituted by a $C_1$ to $C_{10}$ alkyl radical, halogen, hydroxy, protected hydroxy, $C_1$ to $C_4$ alkoxy, carboxy, protected carboxy, amino, or protected amino.

The term "heterocyclic ring" or "heterocycle" denotes optionally substituted five-membered or six-membered rings that have 1 to 4 heteroatoms, such as oxygen, sulfur and/or nitrogen, in particular nitrogen, either alone or in conjunction with sulfur or oxygen ring atoms. These five-membered or six-membered rings may be fully unsaturated or partially unsaturated, with fully unsaturated rings being preferred. Preferred heterocyclic rings include pyridino, pyrimidino, and pyrazino, furano, and thiofurano rings. The heterocyles can be substituted or unsubstituted as, for example, with such substituents as those described in relation to substituted phenyl or substituted naphthyl.

The term "$C_7$ to $C_{16}$ phenylalkyl" denotes a $C_1$ to $C_{10}$ alkyl group substituted at any position by a phenyl ring. Examples of such a group include benzyl, 2-phenylethyl, 3-phenyl-(n-prop-1-yl), 4-phenyl-(-hex-1-yl), 3-phenyl-(n-am-2-yl), 3-phenyl-(sec-butyl), and the like. A preferred group is the benzyl group.

The term "$C_7$ to $C_{16}$ substituted phenylalkyl" denotes a $C_7$ to $C_{16}$ arylalkyl group substituted on the $C_1$ to $C_{10}$ alkyl portion with one or more, and preferably one or two, groups chosen from halogen, hydroxy, protected hydroxy, keto, $C_2$ to $C_3$ cyclic ketal, phenyl, amino, protected amino, $C_1$ to $C_7$ acyloxy, nitro, carboxy, protected carboxy, carbamoyl, carbamoyloxy, cyano, N-(methylsulfonylamino) or $C_1$ to $C_4$ alkoxy; and/or the phenyl group may be substituted with 1 or 2 groups chosen from halogen, hydroxy, protected hydroxy, nitro, $C_1$ to $C_{10}$ alkyl, $C_1$ to $C_6$ substituted alkyl, $C_1$ to $C_4$ alkoxy, carboxy, protected carboxy, carboxymethyl, protected carboxymethyl, hydroxymethyl, protected hydroxymethyl, aminomethyl, protected aminomethyl, amino, (monosubstituted)amino, (disubstituted)amino, a N-(methylsulfonylamino) group, or a phenyl group, substituted or unsubstituted, for a resulting biphenyl group. When either the $C_1$ to $C_{10}$ alkyl portion or the phenyl portion or both are mono- or di-substituted the substituents can be the same or different.

Examples of the term "$C_7$ to $C_{16}$ substituted phenylalkyl" include groups such as 2-phenyl-1-chloroethyl, 2-(4-methoxyphenyl)eth-1-yl, 2,6-dihydroxy-4-phenyl(n-hex-2-yl), 5-cyano-3-methoxy-2-phenyl(n-pent-3-yl), 3-(2,6-dimethylphenyl)n-prop-1-yl, 4-chloro-3-aminobenzyl, 6-(4-methoxyphenyl)-3-carboxy(n-hex-1-yl), 5-(4-aminomethylphenyl)-3-(aminomethyl)(n-pent-2-yl), 5-phenyl-3-keto-(n-pent-1-yl), 4-(4-aminophenyl)-4-(1,4-oxetanyl)(n-but-1-yl), and the like.

The term "$C_7$ to $C_{16}$ phenylalkenyl", denotes a $C_1$ to $C_{10}$ alkenyl group substituted at any position by a phenyl ring. The term "$C_7$ to $C_{16}$ substituted phenylalkenyll" denotes a $C_7$ to $C_{16}$ arylalkyl group substituted on the $C_1$ to $C_{10}$ alkenyl portion. Substituents can the same as those as defined above in relation to $C_7$ to $C_{16}$ phenylalkyl and $C_7$ to $C_{16}$ substituted phenylalkyl. A preferred $C_7$ to $C_{16}$ substituted phenylalkenyl is 3-(4-nitrophenyl)-2-propenyl.

The term "substituted phenyl" specifies a phenyl group substituted with one or more, a one or two, moieties chosen from the groups consisting of halogen, hydroxy, protected hydroxy, cyano, nitro, $C_1$ to $C_{10}$ alkyl, $C_1$ to $C_{10}$ substituted alkyl, $C_1$ to $C_4$ alkoxy, carboxy, protected carboxy, carboxymethyl, protected carboxymethyl, hydroxymethyl, protected hydroxymethyl, amino, protected amino, (monosubstituted)amino, protected (monosubstituted) amino, (disubstituted)amino, trifluoromethyl, N-(methylsulfonylamino), or phenyl, substituted or unsubstituted, such that, for example, a biphenyl results.

Examples of the term "substituted phenyl" includes a mono- or di(halo)phenyl group such as 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl and the like; a mono or di(hydroxy)phenyl groups such as 4-hydroxyphenyl, 3-hydroxyphenyl, 2,4-dihydroxyphenyl, the protected-hydroxy derivatives thereof and the like; a nitrophenyl group such as 3-or 4-nitrophenyl; a cyanophenyl group for example, 4-cyanophenyl; a mono- or di(lower alkyl)phenyl group such as 4-methylphenyl, 2,4-dimethylphenyl, 2-methylphenyl, 4-(iso-propyl)phenyl, 4-ethylphenyl, 3-(n-prop-1-yl)phenyl and the like; a mono or di(alkoxyl)phenyl group, for example, 2,6-dimethoxyphenyl, 4-methoxyphenyl, 3-ethoxyphenyl, 4-(isopropoxy)phenyl, 4-(t-butoxy)phenyl, 3-ethoxy-4-methoxyphenyl, 3-(4-methylphenoxy)phenyl, and the like.; 3-or 4-trifluoromethylphenyl; a mono- or dicarboxyphenyl or (protected carboxy)phenyl group such as 4-carboxyphenyl or 2,4-di(protected carboxy)phenyl; a mono-or di(hydroxymethyl)phenyl or (protected hydroxymethyl) phenyl such as 3-(protected hydroxymethyl)phenyl or 3,4-di(hydroxymethyl)phenyl; a mono- or di(aminomethyl) phenyl or (protected aminomethyl)phenyl such as 2-(aminomethyl)phenyl or 2,4-(protected aminomethyl) phenyl; or a mono- or di(N-(methylsulfonylamino))phenyl such as 3-(N-(methylsulfonylamino))phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy 4-chlorophenyl and the like.

The term "substituted naphthyl" specifies a naphthyl group substituted with one or more, and preferably one or two, moieties chosen from the groups consisting of halogen, hydroxy, protected hydroxy, cyano, nitro, $C_1$ to $C_{10}$ alkyl, $C_1$ to $C_4$ alkoxy, carboxy, protected carboxy, carboxymethyl, protected carboxymethyl, hydroxymethyl, protected hydroxymethyl, amino, protected amino,(monosubstituted) amino, protected (monosubstituted)amino, (disubstituted) amino trifluoromethyl or N-(methylsulfonylamino). Examples of substituted naphthyl include 2-(methoxy)-naphthyl and 4-(methoxy)naphthyl.

The term "substituted indolyl" specifies a indolyl group substituted, either at the nitrogen or carbon, or both, with one or more, and preferably one or two, moieties chosen from the groups consisting of halogen, hydroxy, protected hydroxy, cyano, nitro, $C_1$ to $C_{10}$ alkyl, $C_1$ to $C_{10}$ substituted alkyl, $C_1$ to $C_{10}$ alkenyl, $C_7$ to $C_{16}$ phenylalkyl, $C_7$ to $C_{16}$ substituted phenylalkyl, $C_1$ to $C_6$alkoxy, carboxy, protected carboxy, carboxymethyl, protected carboxymethyl, hydroxymethyl, protected hydroxymethyl, amino, protected amino, monosubstituted amino, or disubstituted amino.

Examples of the term "substituted indolyl" includes such groups as 6-fluoro, 5-fluoro, 5-bromo, 5-hydroxy, 5-methyl, 6-methyl, 7-methyl, 1-methyl, 1-ethyl, 1-benzyl, 1-napth-2-ylmethyl, and the like. An example of a disubstituted indolyl is 1-methyl-5-methyl indolyl.

The terms "halo" and "halogen" refer to the fluoro, chloro, bromo or iodo groups.

The term "(monosubstituted)amino" refers to an amino group with one substituent chosen from the groups consisting of phenyl, substituted phenyl, $C_1$ to $C_{10}$ alkyl, and $C_7$ to $C_{16}$ arylalkyl, wherein the latter three substituent terms are as defined above. The (monosubstituted)amino can additionally have an amino-protecting group as encompassed by the term "protected (monosubstituted)amino."

The term "(disubstituted)amino" refers to amino groups with two substituents chosen from the group consisting of phenyl, substituted phenyl, $C_1$ to $C_{10}$ alkyl, and $C_7$ to $C_{16}$ arylalkyl wherein the latter three substituent terms are as described above. The two substituents can be the same or different.

The terms "(monosubstituted)guanidino," "(disubstituted)guanidino," and "(trisubstituted)guanidino" are where the guanidino groups is substituted with one, two, or three substituents, respectively. The substituents can be any of those as defined above in relation to (monosubstituted)amino and (disubstituted)amino and, where more than one substituent is present, the substituents can be the same or different.

The term "amino-protecting group" as used herein refers to substituents of the amino group commonly employed to block or protect the amino functionality while reacting other functional groups on the amine component. The term "protected (monosubstituted)amino" means there is an amino-protecting group on the monosubstituted amino nitrogen atom. In addition, the term "protected carboxamide" means there is an amino-protecting group replacing the proton so that there is no N-alkylation. Examples of such amino-protecting groups include the formyl ("For") group, the trityl group (Trt), the phthalimido group, the trichloroacetyl group, the chloroacetyl, bromoacetyl, and iodoacetyl groups, urethane-type blocking groups, such as t-butoxycarbonyl ("Boc"), 2-(4-biphenylyl)propyl(2)oxycarbonyl ("Bpoc"), 2-phenylpropyl(2)oxycarbonyl ("Poc"), 2-(4-xenyl)isopropoxycarbonyl, 1,1-diphenylethyl(1)-oxycarbonyl, 1,1-diphenylpropyl(1)oxycarbonyl, 2-(3,5-dimethoxyphenyl) propyl(2)oxycarbonyl ("Ddz"), 2-(p-toluyl) propyl(2)oxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl) ethoxycarbonyl, 2-(methylsulfonyl)ethoxycarbonyl, 2-(triphenylphosphino)-ethoxycarbonyl, 9-fluoroenylmethoxycarbonyl ("Fmoc"), 2-(trimethylsilyl) ethoxycarbonyl, allyloxycarbonyl, 1-(trimethylsilylmethyl) prop-1-enyloxycarbonyl, 5-benz-isoxalylmethoxycarbonyl, 4-acetoxybenzyloxycarbonyl, 2,2,2-trichloroethoxycarbonyl, 2-ethynyl(2) propoxy-carbonyl, cyclopropylmethoxycarbonyl, isobornyl-oxycarbonyl, 1-piperidyloxycarbonyl, benzyloxycarbonyl ("Z"), 4-phenylbenzyloxycarbonyl, 2-methylbenzyloxy-carbonyl, α-2,4,5,-tetramethylbenzyloxycarbonyl ("Tmz"), 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 4-(decyloxy) benzyloxycarbonyl, and the like; the benzoylmethylsulfonyl group, dithiasuccinoyl ("Dts"), the 2-(nitro)phenylsulfenyl group ("Nps"), the diphenyl-phosphine oxide group, and like amino-protecting groups. The species of amino-protecting group employed is not critical so long as the derivatized amino group is stable to the conditions of the subsequent reaction(s) and can be removed at the appropriate point without disrupting the remainder of the compounds. Preferred amino-protecting groups are Boc and Fmoc. Further examples of amino-protecting groups embraced to by the above term are well known in organic synthesis and the peptide art and are described by, for example, T. W. Greene and P. G. M. Wuts, "Protective Groups in Organic Synthesis," 2nd ed., John Wiley and Sons, New York, N.Y., 1991, Chapter 7, M.

Bodanzsky, "Principles of Peptide Synthesis," 1st and 2nd revised ed., Springer-Verlag, New York, N.Y., 1984 and 1993, and Stewart and Young, "Solid Phase Peptide Synthesis," 2nd ed., Pierce Chemical Co., Rockford, Ill., 1984, each of which is incorporated herein by reference. The related term "protected amino" defines an amino group substituted with an amino-protecting group discussed above.

The term "carboxy-protecting group" as used herein refers to one of the ester derivatives of the carboxylic acid group commonly employed to block or protect the carboxylic acid group while reactions are carried out on other functional groups on the compound. Examples of such carboxylic acid protecting groups include 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxytrityl, 4,4',4"-timethoxytrityl, 2-phenylprop-2-yl, trimethylsilyl, t-butyldimethylsilyl, 2,2,2-trichloroethyl, β-(trimethylsilyl) ethyl, β-(di(n-butyl) methylsilyl)ethyl, p-toluenesulfonylethyl, 4-nitrobenzyl-sulfonylethyl, allyl, cinnamyl, 1-(trimethylsilylmethyl)-prop-1-en-3-yl, and like moieties. The species of carboxy-protecting group employed is not critical so long as the derivatized carboxylic acid is stable to the conditions of subsequent reaction(s) and can be removed at the appropriate point without disrupting the remainder of the molecule. Further examples of these groups are found in E. Haslam, "Protective Groups in Organic Chemistry," J. G. W. McOmie, Ed., Plenum Press, New York, N.Y., 1973, Chapter 5, and T. W. Greene and P. G. M. Wuts, "Protective Groups in Organic Synthesis," 2nd ed., John Wiley and Sons, New York, N.Y., 1991, Chapter 5, each of which is incorporated herein by reference. A related term is "protected carboxy," which refers to a carboxy group substituted with one of the above carboxy-protecting groups.

The term "hydroxy-protecting group" refers to readily cleavable groups bonded to hydroxyl groups, such as the tetrahydropyranyl, 2-methoxyprop-2-yl, 1-ethoxyeth-1-yl, methoxymethyl, β-methoxyethoxymethyl, methylthiomethyl, t-butyl, t-amyl, trityl, 4-methoxytrityl, 4,4'-dimethoxytrityl, 4,4',4"-trimethoxytrityl, benzyl, allyl, trimethylsilyl, (t-butyl) dimethylsilyl and 2,2,2-trichloroethoxycarbonyl groups and the like. The species of hydroxy-protecting groups is not critical so long as the derivatized hydroxyl group is stable to the conditions of subsequent reaction(s) and can be removed at the appropriate point without disrupting the remainder of the cyclic urea. Further examples of hydroxy-protecting groups are described by C. B. Reese and E. Haslam, "Protective Groups in Organic Chemistry," J. G. W. McOmie, Ed., Plenum Press, New York, N.Y., 1973, Chapters 3 and 4, respectively, and T. W. Greene and P. G. M. Wuts, "Protective Groups in Organic Synthesis," 2nd ed., John Wiley and Sons, New York, N.Y., 1991, Chapters 2 and 3.

The substituent term "$C_1$ to $C_4$ alkylthio" refers to sulfide groups such as methylthio, ethylthio, n-propylthio, iso-propylthio, n-butylthio, t-butylthio and like groups.

The substituent term "$C_1$ to $C_4$ alkylsulfoxide" indicates sulfoxide groups such as methylsulfoxide, ethylsulfoxide, n-propylsulfoxide, iso-propylsulfoxide, n-butylsulfoxide, sec-butylsulfoxide, and the like.

The term "$C_1$ to $C_4$ alkylsulfonyl" encompasses groups such as methylsulfonyl, ethylsulfonyl, n-propylsulfonyl, iso-propylsulfonyl, n-butylsulfonyl, t-butylsulfonyl, and the like.

Phenylthio, phenyl sulfoxide, and phenylsulfonyl compounds are known in the art and these terms have their art recognized definition. By "substituted phenylthio," "substituted phenyl sulfoxide," and "substituted phenylsulfonyl" is meant that the phenyl can be substituted as described above in relation to "substituted phenyl."

The substituent terms "cyclic $C_2$ to $C_{10}$ alkylene," "substituted cyclic $C_2$ to $C_{10}$ alkylene," "cyclic $C_2$ to $C_{10}$ heteroalkylene," and "substituted cyclic $C_2$ to $C_{10}$ heteroalkylene," defines such a cyclic group bonded ( "fused") to the phenyl radical. The cyclic group may be saturated or contain one or two double bonds. Furthermore, the cyclic group may have one or two methylene groups replaced by one or two oxygen, nitrogen or sulfur atoms.

The cyclic alkylene or heteroalkylene group may be substituted once or twice by substituents selected from the group consisting of the following moieties: hydroxy, protected hydroxy, carboxy, protected carboxy, keto, ketal, $C_1$ to $C_4$ alkoxycarbonyl, formyl, $C_2$ to $C_4$ alkanoyl, $C_1$ to $C_{10}$ alkyl, carbamoyl, $C_1$ to $C_4$ alkoxy, $C_1$ to $C_4$ alkylthio, $C_1$ to $C_4$ alkylsulfoxide, $C_1$ to $C_4$ alkylsulfonyl, halo, amino, protected amino, hydroxymethyl or a protected hydroxymethyl.

The cyclic alkylene or heteroalkylene group fused onto the benzene radical can contain two to ten ring members, but it preferably contains four to six members. Examples of such saturated cyclic groups are when the resultant bicyclic ring system is 2,3-dihydro-indanyl and a tetralin ring. When the cyclic groups are unsaturated, examples occur when the resultant bicyclic ring system is a naphthyl ring or indanyl. An example of a cyclic group which can be fused to a phenyl radical which has two oxygen atoms and which is fully saturated is dioxanyl. Examples of fused cyclic groups which each contain one oxygen atom and one or two double bonds are when the phenyl ring is fused to a furo, pyrano, dihydrofurano, or dihydropyrano ring. Examples of cyclic groups which each have one nitrogen atom and contain one or two double more double bonds are when the phenyl is fused to a pyridino or pyrano ring. An example of a fused ring system having one nitrogen and two phenyl radicals is a carbozoyl group. Examples of cyclic groups which each have one sulfur atom and contain one or two double bonds are when the phenyl is fused to a thieno, thiopyrano, dihydrothieno or dihydrothiopyrano ring. Examples of cyclic groups which contain two heteroatoms selected from sulfur and nitrogen and one or two double bonds are when the phenyl ring is fused to a thiazolo, isothiazolo, dihydrothiazolo or dihydroisothiazolo ring. Examples of cyclic groups which contain two heteroatoms selected from oxygen and nitrogen and one or two double bonds are when the benzene ring is fused to an oxazolo, isoxazolo, dihydrooxazolo or dihydroisoxazolo ring. Examples of cyclic groups which contain two nitrogen heteroatoms and one or two double bonds occur when the benzene ring is fused to a pyrazolo, imidazolo, dihydropyrazolo or dihydroimidazolo ring.

One or more of the cylcic ureas or thioureas within a given library may be present as a pharmaceutically acceptable salt. The term "pharmaceutically-acceptable salt" encompasses those salts that form with the carboxylate anions and ammonium and include salts formed with the organic and inorganic cations discussed below. Furthermore, the term includes salts that form by standard acid-base reactions with basic groups (such as amino groups) and organic or inorganic acids. Such acids include hydrochloric, sulfuric, phosphoric, acetic, succinic, citric lactic, maleic, fumaric, palmitic, cholic, pamoic, mucic, D-glutamic, d-camphoric, glutaric, phthalic, tartaric, lauric, stearic, salicyclic, methanesulfonic, benzenesulfonic, sorbic, picric, benzoic, cinnamic, and like acids.

The term "organic or inorganic cation" refers to counterions for the carboxylate anion of a carboxylate salt. The counter-ions are chosen from the alkali and alkaline earth metals, (such as lithium, sodium, potassium, barium and calcium); ammonium; and the organic cations (such as dibenzylammonium, benzylammonium, 2-hydroxyethylammonium, bis(2-hydroxyethyl)ammonium, phenylethylbenzylammonium, dibebenzylethylenediammonium, and like cations). Other cations encompassed by the above term include the protonated form of procaine, quinine and N-methylglucosamine, and the protonated forms of basic amino acids such as glycine, ornithine, histidine, phenylglycine, lysine and arginine.

Furthermore, any zwitterionic form of the instant compounds formed by a carboxylic acid and an amino group is referred to by this term. A preferred cation for the carboxylate anion is the sodium cation.

The compounds of the above Formula can also exist as solvates and hydrates. Thus, these compounds may crystallize with, for example, waters of hydration, or one, a number of, or any fraction thereof of molecules of the mother liquor solvent. The solvates and hydrates of such compounds are included within the scope of this invention.

One or more cyclic urea or thioureas can be in the biologically active ester form, such as the non-toxic, metabolically-labile ester-form. Such ester forms induce increased blood levels and prolong the efficacy of the corresponding non-esterified forms of the compounds. Ester groups which can be used include the lower alkoxymethyl groups, for example, methoxymethyl, ethoxymethyl, isopropoxymethyl and the like; the α-($C_1$ to $C_4$) alkoxyethyl groups, for example methoxyethyl, ethoxyethyl, propxyethyl, iso-propoxyethyl, and the like; the 2-oxo-1,3-diosolen-4-ylmethyl groups, such as 5-methyl-2-oxo-1, 3-dioxolen-4-ylmethyl, 5-phenyl-2-oxo-1,3-dioxolen-4-ylmethyl, and the like; the $C_1$ to $C_3$ alkylthiomethyl groups, for example methylthiomethyl, ethylthiomethyl, isopropylthiomethyl, and the like; the acyloxymethyl groups, for example pivaloyloxymethyl, pivaloyloxyethyl, α-acetoxymethyl, and the like; the ethoxycarbonyl-1-methyl group; the α-acetoxyethyl; the 3-phthalidyl or 5,6-dimethylphthalidyl groups; the 1-($C_1$ to $C_4$ alkyloxycarbonyloxy)ethyl groups such as the 1-(ethoxycarbonyloxy)ethyl group; and the 1-($C_1$ to $C_4$ alkylaminocarbonyloxy)ethyl groups such as the 1-(methylaminocarbonyloxy)ethyl group.

As used herein, a chemical or combinatorial "library" is an intentionally created collection of differing molecules which can be prepared by the synthetic means provided below or otherwise and screened for biological activity in a variety of formats (e.g., libraries of soluble molecules, libraries of compounds attached to resin beads, silica chips or other solid supports). The libraries can be screened in any variety of assays, such as those detailed below as well as others useful for assessing the biological activity of cyclic ureas and cyclic thioureas. The libraries will generally have at least one active compound and are generally prepared in such that the compounds are in equimolar quantities.

As will be described in further detail, four libraries were prepared, two cyclic urea libraries (X=O), one having $R^2$ as methyl and the other having $R^2$ as benzyl, and two cyclic thioureas (X=S), one having $R^2$ as methyl and the other having $R^2$ as benzyl. For these four libraries, the $R^1$, $R^3$ and $R^4$ positions varied as described above and, in further detail, below. It should be appreciated, however, that such libraries can comprise several smaller "sub-libraries" or sets of mixtures of compounds, depending on the format of preparation and the varying R groups. Sublibraries are described in further detail below.

The cyclic urea and thiourea libraries and compounds of Formula I can be prepared according to the general Reaction Scheme I in FIG. 1. The libraries were prepared using solid-phase techniques. The solid-phase resin, here p-methylbenzhydrylamine resin (MBHA), is indicated in FIG. 1 by the large circle and dash. With reference to Reaction Scheme I, after the addition of a first protected amino acid (having side chain $R^1$) to the resin, the resin is deprotected. Following trityl deprotection, the amide linked to the solid support is selectively N-alkylated (illustrated in FIG. 1). The N-alkylation can be performed using lithium t-butoxide in THF, followed by addition of the alkylating agent in DMSO. The alkylating agents are those which include the $R^2$ groups described above, derivatived with, for example, a bromo, iodo, triflate or methylsulfonate group. Other alkylating derivatives of the group $R^2$ are well known. Preferably the alkylating agent is methyl iodide or benzyl bromide. This method of N-alkylation is known and has been used for the synthesis of soluble peptidomimetic combinatorial libraries through successive or exhaustive amide alkylation as described, for example, in Dorner et al. *Bioorg. & Med. Chem.*, 4:709 (1996) and Ostresh et al. *Proc, Nat. Acad. Sci.*, 91:11138 (1994), both of which are incorporated herein by reference.

Again with reference to Reaction Scheme I in FIG. 1, after N-alkylation, the Trt protecting group is removed with 2% TFA in DCM and a second protected amino acid (having side chain $R^3$) is added using traditional solid phase peptide chemistry. Following deprotection, the resulting dipeptide is then acylated with one of a wide range of available carboxylic acids to obtain the acylated dipeptide. Exemplary amino acid and carboxylic acids are discussed in detail below.

The next key step in the synthetic process, as shown in FIG. 1, is the reduction of the amide groups of the acylated dipeptide using diborane in THF at 65° C. to generate a tertiary and two secondary amines. This method has been used to generate diverse chemical libraries using the "libraries from libraries" concept as described, for instance, in Ostresh et al. *Proc. Nat. Acad. Sci.*, 91:11138 (1994) and Cuervo et al. *In Peptides, 1994, Proceedings of the 23rd European Peptide Symposium* (Maia,H.L.S, ed): 465–466 (1995), each of which are incorporated herein by reference. The cyclizations to obtain the five-member ring (and six-member ring when $R^3$ is β-Ala and, therefore, n is two) cyclic ureas and cyclic thioureas were performed using carbonyldiimidazole and thiocarbonyldiimidazole as described in the ensuing Example. Alternatively, the cyclization step can carried out using phosgene, triphosgene or thiophosgene by the procedures described, for example, in Majer and Randad, *J. Org. Chem.*, 59:1937–1938 (1994), and Kim et al., *Tetrahedron Lett.*, 37:5309 (1996), both of which are incorporated herein by reference.

Any variety of amino acids can be used with the present invention as described above to generate a vast array of cyclic ureas and thioureas with different $R^1$ and $R^3$ groups. As described in the ensuing Example, forty different first amino acids were coupled to the resin, which amino acids contain $R^1$. The forty amino acids included Ala, Phe, Gly, Ile, Lys(Boc), Leu, Met(O), Asn, Gln, Arg(Pmc), Ser(tBu), Thr(tBu), Val, Trp, Tyr(Brz), Tyr(tBu), ala, phe, ile, lys (Boc), leu, asn, gin, ser, thr(tBu), val, trp, tyr(tBu), arg (Pmc), Nle, nle, Nva, nva, Nap, nap, Phg, Cha, cha, His(Trt) and his(Trt). After the above described N-alkylation, thirty seven different second amino acids were coupled, thereby providing thirty seven various $R^3$ groups. Those thirty seven amino acids included Ala, Phe, Gly, Ile, Leu, Met(O), Arg(Pmc), Ser(tBu), Thr(tBu),Val, Trp(Boc), Tyr(Brz), Tyr (tBu), ala, phe, ile, leu, ser, thr(tBu), val, trp(Boc), tyr(tBu), arg(Pmc), Nle, nle, Nva, nva, Nap, nap, Phg, Glu(tBu), glu(tBu), β-Ala, Cha, cha, His(Trt) and his(Trt).

As used herein, abbreviations for the various amnio acid side-chain protecting groups are as follows: "Trt" for trityl, "tBu" for tert-butyl, "Boc" for tert-butoxycarbonyl, "Brz" for 2-bromobenzyloxycarbonyl, and "Pmc" for 2,2,5,7,8-pentamethylchroman-6-sulfonyl. These abbreviations and any others used herein are those which are commonly known and used in the field. Moreover, also as is commonly practiced in the field and with reference to the amino acid nomenclature, all lower case lettering herein means the D-form of the amino acid as opposed to the L-form. Other nomenclature and three-letter abbreviations used herein for amino acids and derivatives thereof, as well as their respective side chains are as follows:

TABLE 1

| AMINO ACID NAME | | |
|---|---|---|
| FULL | 3-LETTER CODE | SIDE CHAIN R (FOR $R^1$ AND $R^3$) |
| Glycine | Gly | —H |
| Alanine | Ala | —CH₃ |
| Valine | Val | —CH(CH₃)₂ |
| Leucine | Leu | —CH₂CH(CH₃)₂ |
| Isoleucine | Ile | —CH(CH₃)CH₂CH₃ |
| Lysine | Lys | —(CH₂)₄NH₂ |
| Arginine | Arg | —CH₂CH₂CH₂NHC(NH)NH₂ |
| Glutamic Acid | Glu | —CH₂CH₂COOH |
| Serine | Ser | —CH₂OH |
| Threonine | Thr | —CH(OH)CH₃ |
| Phenylalanine | | 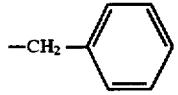 |
| Tyrosine | Tyr | 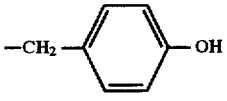 |
| Tryptophan | Trp | 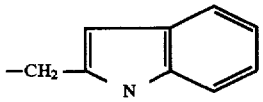 |
| β-Alanine | β-Ala | —CH₂—CH₂— |
| Norvaline | Nva | —CH₂CH₂CH₃ |
| Norleucine | Nle | —CH₂CH₂CH₂CH₃ |
| Napthylalanine | Nap | 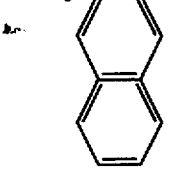 |
| Cyclohexylalanine | Cha | 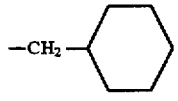 |
| Methionine | Met | —CH₂CH₂—S—CH₃ |
| Asparagine | Asn | —CH₂C(O)NH₂ |
| Glutamine | Gln | —CH₂CH₂C(O)NH₂ |
| Histidine | His | 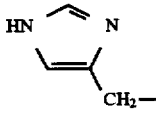 |
| Phenylglycine | Phg | 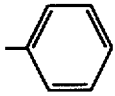 |

As can be seen from the side chains exemplified in the above Table, n in Formula I in all preferred instances is 1, the α-carbon, except when β-Alanine is used, in which case n is 2 and the core ring of the urea will be enlarged to a six-membered ring.

It should be appreciated from the above-described embodiments of $R^1$ and $R^3$, as well as from the described reaction scheme, that some of the amino acid side chains are modified during the synthesis. For instance some of the RI amino acid side chains are modified by the N-alkylation and/or the reduction steps. Similarly, certain $R^3$ groups are modified by the reduction procedures. Accordingly, with reference to the forty preferred embodiments of $R^1$ and the thirty seven of $R^3$, they are described above and below, except in Table I, in their modified form. A specific example of a modified lysine side chain is provided in Example II below.

As well, a variety of carboxylic acids can be used in the acylation step of Reaction Scheme I, thereby generating a wide array of substituents at the $R^4$ position of the cyclic ureas and thioureas. Preferably, eighty carboxylic acids were used in preparing the subject libraries and compounds. Those eighty carboxylic acids were 1-phenyl-1-cyclopropanecarboxylic acid, 2-phenylbutyric acid, 3-phenylbutyric acid, m-tolylacetic acid, 3-fluorophenylacetic acid, 3-bromophenylacetic acid, ($\alpha,\alpha$, $\alpha$-trifluoro-m-tolyl)acetic acid, p-tolylacetic acid, 4-fluorophenylacetic acid, 3-methoxyphenylacetic acid, 4-bromophenylacetic acid, 4-methoxyphenylacetic acid, 4-ethoxyphenylacetic acid, 4-isobutyl-$\alpha$-methylphenylacetic acid, 3,4-dichlorophenylacetic acid, 3,5-bis(trifluoromethyl) phenylacetic acid, 3-(3,4-dimethoxyphenyl) propionic acid, 4-biphenylacetic acid, $\alpha$-methylcinnamic acid, 2-(trifluoromethyl)cinnamic acid, (3,4-dimethoxyphenyl)acetic acid, 3,4-(methylenedioxy) phenylacetic acid, 2-methoxycinnamic acid, benzoic acid, 4-chlorocinnamic acid, trans-cinnamic acid, m-toluic acid, phenylacetic acid, hydrocinnamic acid, 4-phenylbutyric acid, 3,5-bis(trifluoromethyl)benzoic acid, butyric acid, heptanoic acid, isobutyric acid, (+/−)-2-methylbutyric acid, isovaleric acid, 3-methylvaleric acid, 4-methylvaleric acid, crotonic acid, vinylacetic acid, p-toluic acid, trimethylacetic acid, tert-butylacetic acid, cyclohexanecarboxylic acid, cyclohexylacetic acid, cyclohexanebutyric acid, cycloheptanecarboxylic acid, acetic acid, 2-methylcyclopropanecarboxylic acid, cyclobutanecarboxylic acid, cyclopentanecarboxylic acid, 3-cyclopentylpropionic acid, cyclohexanepropionic acid, 4-methyl-1-cyclohexanecarboxylic acid, 4-tert-butylcyclohexanecarboxylic acid, 4-methylcyclohexaneacetic acid, tiglic acid, 1-adamantaneacetic acid, niflumic acid, 4-nitrophenylacetic acid, 4-(nitrophenyl)butyric acid, 4-nitrocinnamic acid, 2-nitrobenzoic acid, 2,4-dinitrophenylacetic acid, 4-biphenylacetic acid, 2-chloro-5-nitrobenzoic acid, (4-pyridilthio)acetic acid, 3-3-diphenylpropionic acid, 2-chloro-4-nitrobenzoic acid, 4-dimethylaminobenzoic acid, 4-nitrobenzoic acid, 3-dimethylbenzoic acid, abietic acid, 2-methyl-4-nitro-1-imidizolepropionic acid, trans-styrylacetic acid, cyclopentylacetic acid, dicyclohexylacetic acid, (2-pyridithio)acetic acid, pentadienoicacid, and indole-3-acetic acid.

The nonsupport-bound library mixtures were screened in solution in radio-receptor inhibition assays and an antibacterial assay described in detail below. Deconvolution of highly active mixtures can then be carried out by iterative, or positional scanning methods. These techniques, the iterative approach or the positional scanning approach, can be utilized for finding other active compounds within the libraries of the present invention using any one of the below-described assays or others well known in the art.

The iterative approach is well-known and is set forth in general in Houghten et al., *Nature*, 354, 84–86 (1991) and Dooley et al., *Science*, 266, 2019–2022 (1994), both of which are incorporated herein by reference. In the iterative approach, for example, sub-libraries of a molecule having three variable groups are made wherein the first variable is defined. Each of the compounds with the defined variable group is reacted with all of the other possibilities at the other two variable groups. These sub-libraries are each tested to define the identity of the second variable in the sub-library having the highest activity in the screen of choice. A new sub-library with the first two variable positions defined is reacted again with all the other possibilities at the remaining undefined variable position. As before, the identity of the third variable position in the sub-library having the highest activity is determined. If more variables exist, this process is repeated for all variables, yielding the compound with each variable contributing to the highest desired activity in the screening process. Promising compounds from this process can then be synthesized on larger scale in traditional single-compound synthetic methods for further biological investigation.

The positional-scanning approach has been described for various libraries as described, for example, in R. Houghten et al. PCT/US91/08694 and U.S. Pat. No. 5,556,762, both of which are incorporated herein by reference. The positional scanning approach is used as described below in the preparation and screening of the libraries. In the positional scanning approach sublibraries are made defining only one variable with each set of sublibraries- and all possible sublibraries with each single variable defined (and all other possibilities at all of the other variable positions) is made and tested. From the instant description one skilled in the art could synthesize libraries wherein 2 fixed positions are defined at a time. From the testing of each single-variable defined library, the optimum substituent at that position is determined, pointing to the optimum or at least a series of compounds having a maximum of the desired biological activity. Thus, the number of sublibraries for compounds with a single position defined will be the number of different substituents desired at that position, and the number of all the compounds in each sublibrary will be the product of the number of substituents at each of the other variables.

Individual compounds and pharmaceutical compositions containing the new cyclic ureas and thioureas, as well as methods of using the same are included within the scope of the present invention. The new urea compounds of the present invention can be used for a variety of purposes and indications and as medicaments for any such purposes and indications. For example, cyclic urea moieties are found in many biologically active compounds and, as described above, have even been used as potent inhibitors of HIV protease and HIV replication.

Moreover, as shown in Example IV, cyclic thioureas of the present invention have antimicrobial activity. Thus the ureas of the present invention can be used to treat infections. The ability of the compounds to inhibit bacterial growth can be determined by methods well known in the art. An exemplary in vitro antimicrobial activity assay is described in Blondelle and Houghten, *Biochemistry* 30:4671–4678 (1991), which is incorporated herein by reference. In brief, *Staphylococcus aureus* ATCC 29213 (Rockville, Md.) is grown overnight at 37° C. in Mueller-Hinton broth, then re-inoculated and incubated at 37° C. to reach the exponential phase of bacterial growth (i.e., a final bacterial suspension containing $10^5$ to $5 \times 10^5$ colony-forming units/ml). The concentration of cells is established by plating 100 μl of the culture solution using serial dilutions (e.g., $10^{-2}$, $10^{-3}$ and $10^{-4}$) onto solid agar plates. In 96-well tissue culture plates cyclic ureas, individual or in mixtures, are added to the bacterial suspension at concentrations derived from serial two-fold dilutions ranging from 1500 to 2.9 μg/ml. The plates are incubated overnight at 37° C. and the growth determined at each concentration by $OD_{620}$ nm. The $IC_{50}$ (the concentration necessary to inhibit 50% of the growth of the bacteria) can then be calculated.

Additional assays can be, and have been, used to test the biological activity of the instant ureas. Such assays include a competitive enzyme-linked immunoabsorbent assay and, as described in Example IV, radio-receptor assays. The latter test, the radio-receptor assay, can be selective for any one of the μ, κ, or δ opiate receptors and is, therefore, an indication of ureas+ analgesic properties as described, for example, in Dooley et al., *Proc. Natl. Acad. Sci.*, 90:10811–10815 (1993). Additionally, such compounds can be tested in a σ receptor assay. Ligands for the σ receptor can be useful as antipsychotic agents, as described in Abou-Gharbia et al., *Annual Reports in Medicinal Chemistry*, 28:1–10 (1993).

Competitive Enzyme-Linked Immunosorbent Assay (ELISA): The competitive ELISA method which can be used here is a modification of the direct ELISA technique described previously in Appel et al., *J. Immunol.* 144:976–983 (1990), which is incorporated herein by reference. It differs only in the MAb addition step. Briefly, multi-well microplates are coated with the antigenic peptide (Ac-GASPYPNLSNQQT-$NH_2$) at a concentration of 100 pmol/50 μL. After blocking, 25 μl of a 1.0 mg/ml solution of each urea mixture of a synthetic combinatorial library (or individual urea) is added, followed by MAb 125-10F3 (Appel et al., supra) (25 μl per well). The MAb is added at a fixed dilution in which the urea in solution effectively competes for MAb binding with the antigenic peptide adsorbed to the plate. The remaining steps are the same as for direct ELISA. The concentration of urea necessary to inhibit 50% of the MAb binding to the control peptide on the plate ($IC_{50}$) is determined by serial dilutions of the cyclic urea.

Radio-Receptor Assay: Particulate membranes can be prepared using a modification of the method described in Pasternak et al., *Mol. Pharmacol.* 11:340–351 (1975), which is incorporated herein by reference. Rat brains frozen in liquid nitrogen can be obtained from Rockland (Gilbertsville, Pa.). The brains are thawed, the cerebella removed and the remaining tissue weighed. Each brain is individually homogenized in 40 ml Tris-HCl buffer (50 mM, pH 7.4, 4° C.) and centrifuged (Sorvall ® RC5C SA-600: Du Pont, Wilmington, Del.) (16,000 rpm) for 10 mins. The pellets are resuspended in fresh Tris-HCl buffer and incubated at 37° C. for 40 mins. Following incubation, the suspensions are centrifuged as before, the resulting pellets resuspended in 100 volumes of Tris buffer and the suspensions combined. Membrane suspensions are prepared and used in the same day. Protein content of the crude homogenates generally range from 0.15–0.2 mg/ml as determined using the method described in M. M. Bradford, M. M., *Anal. Biochem.* 72:248–254 (1976), which is incorporated herein by reference.

Binding assays are carried out in polypropylene tubes, each tube containing 0.5 ml of membrane suspension. 8 nM of $^3$H-[D-$Ala^2$, Me-$Phe^4$, Gly-$ol^5$] enkephalin (DAMGO) (specific activity=36 Ci/mmol, 160,000 cpm per tube; which can be obtained from Multiple Peptide Systems, San Diego, Calif., through NIDA drug distribution program 271-90-7302) and 80 μg/ml of urea, individual or as a mixture and Tris- HCl buffer in a total volume of 0.65 ml. Assay tubes are incubated for 60 mins. at 25° C. The reaction is terminated by filtration through GF-B filters on a Tomtec harvester (Orange, Conn.). The filters are subsequently washed with 6 ml of Tris- HCl buffer, 4° C. Bound radioactivity is counted on a Pharmacia Biotech Betaplate Liquid Scintillation Counter (Piscataway, N.J.) and expressed in cpm. To determine inter- and intra -assay variation, standard curves in which $^3$H-DAMGO is incubated in the presence of a range of concentrations of unlabeled DAMGO (0.13–3900 nM) are generally included in each plate of each assay (a 96-well format). Competitive inhibition assays are performed as above using serial dilutions of the ureas, individually or in mixtures. $IC_{50}$ values (the concentration necessary to inhibit 50% of $^3$H-DAMGO binding) are then calculated. As opposed to this μ receptor selective assay, assays selective for κ receptors can be carried out using [$^3$H]-U69,593 (3 nM, specific activity 62 Ci/mmol) as radioligand. Assays selective for δ opiate receptors can be carried out using tritiated DSLET ([D-$Ser^2$, D-$Leu^5$]-threonine-enkephalin) as radioligand. Similarly, assays for the σ a receptor assay are the same as the μ assay but use radiolabeled pentazocine as ligand.

As pharmaceutical compositions for treating infections, pain, or other indications known to be treatable by cyclic ureas or thioureas, the urea compounds of the present invention are generally in a pharmaceutical composition so as to be administered to a subject at dosage levels of from 0.7 to 7000 mg per day, and preferably 1 to 500 mg per day, for a normal human adult of approximately 70 kg of body weight, this translates into a dosage of from 0.01 to 100 mg/kg of body weight per day. The specific dosages employed, however, can be varied depending upon the requirements of the patient, the severity of the condition being treated, and the activity of the compound being employed. The determination of optimum dosages for a particular situation is within the skill of the art.

For preparing pharmaceutical compositions containing compounds of the invention, inert, pharmaceutically acceptable carriers are used. The pharmaceutical carrier can be either solid or liquid. Solid form preparations include, for example, powders, tablets, dispersible granules, capsules, cachets, and suppositories.

A solid carrier can be one or more substances which can also act as diluents, flavoring agents, solubilizers, lubricants, suspending agents, binders, or tablet disintegrating agents; it can also be an encapsulating material.

In powders, the carrier is generally a finely divided solid which is in a mixture with the finely divided active component. In tablets, the active compound is mixed with the carrier having the necessary binding properties in suitable proportions and compacted in the shape and size desired.

For preparing pharmaceutical composition in the form of suppositories, a low-melting wax such as a mixture of fatty acid glycerides and cocoa butter is first melted and the active ingredient is dispersed therein by, for example, stirring. The molten homogeneous mixture is then poured into convenient-sized molds and allowed to cool and solidify.

Powders and tablets preferably contain between about 5% to about 70% by weight of the active ingredient. Suitable carriers include, for example, magnesium carbonate, magnesium stearate, talc, lactose, sugar, pectin, dextrin, starch, tragacanth, methyl cellulose, sodium carboxymethyl cellulose, a low-melting wax, cocoa butter and the like.

The pharmaceutical compositions can include the formulation of the active compound with encapsulating material as a carrier providing a capsule in which the active component (with or without other carriers) is surrounded by a carrier, which is thus in association with it. In a similar manner, cachets are also included.

Tablets, powders, cachets, and capsules can be used as solid dosage forms suitable for oral administration.

Liquid pharmaceutical compositions include, for example, solutions suitable for oral or parenteral administration, or suspensions, and emulsions suitable for oral administration. Sterile water solutions of the active component or sterile solutions of the active component in solvents comprising water, ethanol, or propylene glycol are examples of liquid compositions suitable for parenteral administration.

Sterile solutions can be prepared by dissolving the active component in the desired solvent system, and then passing the resulting solution through a membrane filter to sterilize it or, alternatively, by dissolving the sterile compound in a previously sterilized solvent under sterile conditions.

Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethyl cellulose, and other suspending agents known to the pharmaceutical formulation art.

Preferably, the pharmaceutical composition is in unit dosage form. In such form, the composition is divided into unit doses containing appropriate quantities of the active urea. The unit dosage form can be a packaged preparation, the package containing discrete quantities of the preparation, for example, packeted tablets, capsules, and powders in vials or ampules. The unit dosage form can also be a capsule, cachet, or tablet itself, or it can be the appropriate number of any of these packaged forms.

The following Examples are intended to illustrate but not limit the present invention.

EXAMPLE I

This example provides the synthesis of four combinatorial libraries of the present invention; (1) X=O, R$^2$=methyl, (2) X=O, R$^2$=benzyl, (3) X=S, R$^2$=methyl and (4) X=S, R$^2$=benzyl. The R$^1$, R$^3$ and R$^4$ groups varied as described above and below. Again, forty first amino acids were used, generating at least forty R$^1$ groups, depending on the modifications to the side chains. The amino acids used to generate R$^1$ are again listed below in Table 2. Thirty-seven second amino acids were used to generate the various R$^3$ groups, which amino acids are also again summarized in Table 2 below. Finally the eighty carboxylic acids used to acylate the dipeptides and generate R$^4$ are also listed again in Table 2. Therefore, Table 2 provides a summary of all the amino acids (R$^1$ and R$^3$), alkylation moieties (R$^2$) and carboxylic acid components (R$^4$) used in the preparation of the libraries.

TABLE 2

SUMMARY OF R GROUPS IN PREPARED LIBRARIES

| | R$^1$ | R$^2$ | R$^3$ | R$^4$ |
|---|---|---|---|---|
| 1 | Ala | Me | Ala | 1-phenyl-1-cyclopropane-carboxylic acid |
| 2 | Phe | Bzl | Phe | 2-phenylbutyric acid |
| 3 | Gly | | Gly | 3-phenylbutyric acid |
| 4 | Ile | | Ile | m-tolylacetic acid |
| 5 | Lys (Boc) | | Leu | 3-fluorophenylacetic acid |
| 6 | Leu | | Met (O) | 3-bromophenylacetic acid |
| 7 | Met (O) | | Arg (Pmc) | (α,α,α-trifluoro-m-tolyl)acetic acid |
| 8 | Asn | | Ser (tBu) | p-tolylacetic acid |
| 9 | Gln | | Thr (tBu) | 4-fluorophenylacetic acid |
| 10 | Arg (Pmc) | | Val | 3-methoxyphenylacetic acid |
| 11 | Ser | | Trp | 4-bromophenylacetic acid |

TABLE 2-continued

SUMMARY OF R GROUPS IN PREPARED LIBRARIES

| | R$^1$ | R$^2$ | R$^3$ | R$^4$ |
|---|---|---|---|---|
| 12 | Thr (tBu) | | Tyr (Brz) | 4-methoxyphenylacetic acid |
| 13 | Val | | Tyr (tBu) | 4-ethoxyphenylacetic acid |
| 14 | Trp | | ala* | 4-isobutyl-α-methylphenylacetic acid |
| 15 | Tyr (Brz) | | phe | 3,4-dichlorophenylacetic acid |
| 16 | Tyr (tBu) | | ile | 3,5-bis(trifluoromethyl)phenylacetic acid |
| 17 | ala | | leu | 3-(3,4-dimethoxyphenyl)propionic acid |
| 18 | phe | | ser | 4-biphenylacetic acid |
| 19 | ile | | thr (tBu) | α-methylcinnamic acid |
| 20 | lys (Boc) | | val | 2-(trifluoromethyl)cinnamic acid |
| 21 | leu | | trp (Boc) | (3,4-dimethoxyphenyl)acetic acid |
| 22 | asn | | try (tBu) | 3,4-(methylenedioxy)phenylacetic acid |
| 23 | gln | | arg (Pmc) | 2-methoxycinnamic acid |
| 24 | ser | | Nle | benzoic acid |
| 25 | thr (tBu) | | nle | 4-chlorocinnamic acid |
| 26 | val | | Nva | trans-cinnamic acid |
| 27 | trp | | nva | m-toluic acid |
| 28 | tyr (tBu) | | Nap | phenylacetic acid |
| 29 | arg (Pmc) | | nap | hydrocinnamic acid |
| 30 | Nle | | Phg | 4-phenylbutyric acid |
| 31 | nle | | Glu (tBu) | 3,5-bis(trifluoromethyl)benzoic acid |
| 32 | Nva | | glu (tBu) | butyric acid |
| 33 | nva | | βAla | heptanoic acid |
| 34 | Nap | | Cha | isobutyric acid |
| 35 | nap | | cha | (+/−)-2-methylbutyric acid |
| 36 | Phg | | His (Trt) | isovaleric acid |
| 37 | Cha | | his (Trt) | 3-methylvaleric acid |
| 38 | cha | | | 4-methylvaleric acid |
| 39 | His (Trt) | | | crotonic acid |
| 40 | his (Trt) | | | vinylacetic acid |
| 41 | | | | p-toluic acid |
| 42 | | | | trimethylacetic acid |
| 43 | | | | tert-butylacetic acid |
| 44 | | | | cyclohexanecarboxylic acid |
| 45 | | | | cyclohexylacetic acid |
| 46 | | | | cyclohexanebutyric acid |
| 47 | | | | cycloheptanecarboxylic acid |
| 48 | | | | acetic acid |
| 49 | | | | 2-methylcyclopropanecarboxylic acid |
| 50 | | | | cyclobutanecarboxylic acid |
| 51 | | | | cyclopentanecarboxylic acid |
| 52 | | | | 3-cyclopentylpropionic acid |
| 53 | | | | cyclohexanepropionic acid |
| 54 | | | | 4-methyl-1-cyclohexanecarboxylic acid |
| 55 | | | | 4-tert-butylcyclohexanecarboxylic acid |
| 56 | | | | 4-methylcyclohexaneacetic acid |
| 57 | | | | tiglic acid |
| 58 | | | | 1-adamantaneacetic acid |
| 59 | | | | niflumic acid |
| 60 | | | | 4-nitrophenyl acetic acid |
| 61 | | | | 4-(nitrophenyl)butyric acid |
| 62 | | | | 4-nitrocinnamic acid |
| 63 | | | | 2-nitrobenzoic acid |
| 64 | | | | 2,4-dinitrophenyl acetic acid |
| 65 | | | | 4-biphenyl acetic acid |
| 66 | | | | 2-chloro-5-nitrobenzoic acid |
| 67 | | | | (4-pyridylthio)acetic acid |

TABLE 2-continued

SUMMARY OF R GROUPS IN PREPARED LIBRARIES

| | $R^1$ | $R^2$ | $R^3$ | $R^4$ |
|---|---|---|---|---|
| 68 | | | | 3-3 diphenyl propionic acid |
| 69 | | | | 2-chloro-4-nitrobenzoic acid |
| 70 | | | | 4-dimethylaminobenzoic acid |
| 71 | | | | 4-nitrobenzoic acid |
| 72 | | | | 3-dimethylaminobenzoic acid |
| 73 | | | | abietic acid |
| 74 | | | | 2-methyl-4-nitro-1-imidizole propionic acid |
| 75 | | | | trans-styryl acetic acid |
| 76 | | | | cyclopentyl acetic acid |
| 77 | | | | dicyclohexyl acetic acid |
| 78 | | | | (2-pyridylthio)acetic acid |
| 79 | | | | pentadienoic acid |
| 80 | | | | indole-3-acetic acid |

*lower case lettering indicates D-amino acids

Pools of libraries were prepared in the positional scan format. A typical procedure for the combinatorial synthesis of the subject cyclic ureas and cyclic thioureas libraries was as follows. One hundred and eighty mg of p-methylbenzhydrylamine (MBHA) resin (0.81 meq/g, 100–200 mesh) was contained within a sealed polypropylene mesh packet. Reactions were carried out in a 10 ml polyethylene bottle. Following neutralization with 5% diisopropylethylamine (DIEA) in dichloromethane (DCM), the resin was washed with DCM. The first amino acid (Fmoc-Xaa-OH in FIG. 1) was coupled using the conventional reagents hydroxybenzotriazole (HOBt) and diisopropylcarbodiimide (DICI). Following removal of the protecting group with 25% piperidine in DMF, the mesh packet was shaken overnight in a solution of trityl chloride in DCM/DMF (9:1) in the presence of DIEA. Completeness of the trityl coupling was verified using the bromophenol blue color test as described in (Krchnak et al. *Coll. Czech. Chem. Commun.*, 53:2542 (1988), which is incorporated herein by reference.

N-alkylation was then performed by treatment of the resin packet with 1M lithium t-butoxide in THF. Excess base was removed by cannulation, followed by addition of the individual alkylating agent in DMSO. The solution was vigorously shaken for 2 h at room temperature. Upon removal of the trityl group with 2% TFA in DCM (2×10 min), the packet was washed, neutralized and the second amino acid (Fmoc-Xaa-OH in FIG. 1) coupled. Following removal of the Fmoc group, the dipeptide was individually acylated with a carboxylic acid in the presence of diisopropylcarbodiimide (DICI) and 1-hydroxybenzotriazole (HOBt).

The reductions were performed in 50 ml kimax tubes under nitrogen. Boric acid (40×) and trimethyl borate (40×) were added, followed by 1M $BH_3$-THF (40×). The tubes were heated at 65° C. for 72 h, followed by quenching with MeOH. The resin was then washed with tetrahydrofuran and methanol. The amine-borane complex was disassociated by overnight treatment with piperdine at 65° C.

The cyclization occurred following treatment of the reduced acylated dipeptide overnight with carbonyldiimidazole (0.5M in dichloromethane anhydrous) for cyclic urea formation and thiocarbonyldiimidazole (0.5M in dichloromethane anhydrous) for thiourea formation. Following cleavage from the resin with anhydrous HF by the procedures of Houghten et al. *Int. J. Pep. Prot. Res.*, 27:673 (1986), which is incorporated herein by reference, in the presence of anisole, the desired products were extracted and lyophilized. The desired products were obtained in good yields and high purity (>90% by HPLC)following lyophilization.

EXAMPLE II

FIG. 2 provides the RP-HPLC and LCQ-Mass spectra of the cyclic urea (X=O) (expected mass: 498) and cyclic thiourea (X=S) (expected mass: 514), with: $R^2$=Bzl, $R^1$=modified side chain of lysine, $R^3$=side chain of alanine, $R^4$=benzyl (benzoic acid before reduction) and n=one. This thiourea, and its modified lysine side chain are provided below.

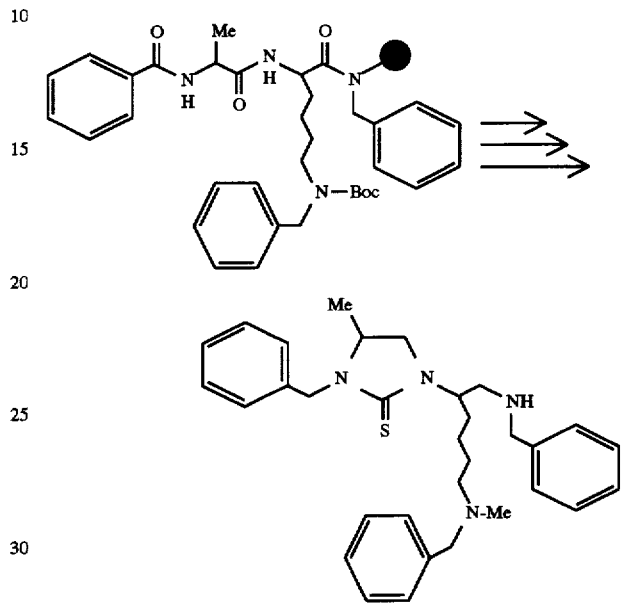

EXAMPLE III

Following the procedures of Example I, the following pools of libraries containing N-benzyl aminocyclic thioureas were prepared by the positional scan format. Therefore, X=S and $R^2$=benzyl and the remaining R groups and their respective pool reference numbers are identified in Table 3 below. Each of the 157 pools were screened in an anti-microbial assay and μ and κ-opioid receptor assays as provided in Example IV. This Example and Table 3 is provided for further reference for pool compositions in relation to the biological data in the ensuing Example.

TABLE 3

LIBRARY POOL REFERENCE NUMBERS AND VARIABLE R GROUPS FOR N-BENZYL AMINOCYCLIC THIOUREA LIBRARY

| Pool No. | $R^1$ | $R^3$ | $R^4$ |
|---|---|---|---|
| 1 | X | X | 1-phenyl-1-cyclopropanecarboxylic acid |
| 2 | X | X | 2-phenylbutyric acid |
| 3 | X | X | 3-phenylbutyric acid |
| 4 | X | X | m-tolylacetic acid |
| 5 | X | X | 3-fluorophenylacetic acid |
| 6 | X | X | 3-bromophenylacetic acid |
| 7 | X | X | (α,α,α-trifluoro-m-tolyl) acetic acid |
| 8 | | X | p-tolylacetic acid |
| 9 | X | | 4-fluorophenylacetic acid |
| 10 | | X | 3-methoxyphenylacetic acid |
| 11 | X | X | 4-bromophenylacetic acid |
| 12 | X | X | 4-methoxyphenylacetic acid |
| 13 | X | X | 4-ethoxyphenylacetic acid |
| 14 | X | X | 4-isobutyl-α-methylphenylacetic |

TABLE 3-continued

LIBRARY POOL REFERENCE NUMBERS AND VARIABLE R GROUPS FOR N-BENZYL AMINOCYCLIC THIOUREA LIBRARY

| Pool No. | $R^1$ | $R^3$ | $R^4$ |
|---|---|---|---|
| 15 | X | X | 3,4-dichlorophenylacetic acid |
| 16 | X | X | 3,5-bis(trifluoromethyl)phenylacetic acid |
| 17 | X | X | 3-(3,4-dimethoxyphenyl)propionic acid |
| 18 | X | X | 4-biphenylacetic acid |
| 19 | X | X | α-methylcinnamic acid |
| 20 | X | X | 2-(trifluoromethyl)cinnamic acid |
| 21 | X | X | (3,4-dimethoxyphenyl)acetic acid |
| 22 | X | X | 3,4-(methylenedioxy)phenylacetic acid |
| 23 | X | X | 2-methoxycinnamic acid |
| 24 | X | X | benzoic acid |
| 25 | X | X | 4-chlorocinnamic acid |
| 26 | X | X | trans-cinnamic acid |
| 27 | X | X | m-toluic acid |
| 28 | X | X | phenylacetic acid |
| 29 | X | X | hydrocinnamic acid |
| 30 | X | X | 4-phenylbutyric acid |
| 31 | X | X | 3,5-bis(trifluoromethyl)benzoic acid |
| 32 | X | X | butyric acid |
| 33 | X | X | heptanoic acid |
| 34 | X | X | isobutyric acid |
| 35 | X | X | (+/−)-2-methylbutyric acid |
| 36 | X | X | isovaleric acid |
| 37 | X | X | 3-methylvaleric acid |
| 38 | X | X | 4-methylvaleric acid |
| 39 | X | X | crotonic acid |
| 40 | X | X | vinylacetic acid |
| 41 | X | X | p-toluic acid |
| 42 | X | X | trimethylacetic acid |
| 43 | X | X | tert-butylacetic acid |
| 44 | X | X | cyclohexanecarboxylic acid |
| 45 | X | X | cyclohexylacetic aaid |
| 46 | X | X | cyclohexanebutyric acid |
| 47 | X | X | cycloheptanecarboxylic acid |
| 48 | X | X | acetic acid |
| 49 | X | X | 2-methylcyclopropanecarboxylic acid |
| 50 | X | X | cyclobutanecarboxylic acid |
| 51 | X | X | cyclopentanecarboxylic acid |
| 52 | X | X | 3-cyclopentylpropionic acid |
| 53 | X | X | cyclohexanepropionic acid |
| 54 | X | X | 4-methyl-1-cyclohexanecarboxylic acid |
| 55 | X | X | 4-tert-butylcyclohexanecarboxylic acid |
| 56 | X | X | 4-methylcyclohexaneacetic acid |
| 57 | X | X | tiglic acid |
| 58 | X | X | 1-adamantaneacetic acid |
| 59 | X | X | niflumic acid |
| 60 | X | X | 4-nitrophenyl acetic acid |
| 61 | X | X | 4-(nitrophenyl)butyric acid |
| 62 | X | X | 4-nitrocinnamic acid |
| 63 | X | X | 2-nitrobenzoic acid |
| 64 | X | X | 2,4-dinitrophenyl acetic acid |
| 65 | X | X | 4-biphenyl acetic acid |
| 66 | X | X | 2-chloro-5-nitrobenzoic acid |
| 67 | X | X | (4-pyridylthio)acetic acid |
| 68 | X | X | 3-3 diphenyl propionic acid |
| 69 | X | X | 2-chloro-4-nitrobenzoic acid |
| 70 | X |  | 4-dimethylaminobenzoic acid |
| 71 | X | X | 4-nitrobenzoic acid |
| 72 | X | X | 3-dimethylaminobenzoic acid |
| 73 | X | X | abietic acid |
| 74 | X | X | 2-methyl-4-nitro-1-imidizole propionic acid |
| 75 | X | X | trans-styryl acetic acid |
| 76 | X | X | cyclopentyl acetic acid |
| 77 | X | X | dicyclohexyl acetic acid |
| 78 | X | X | (2-pyridylthio)acetic acid |
| 79 | X | X | pentadienoic acid |
| 80 | X | X | indole-3-acetic acid |
| 81 | X | Ala | X |
| 82 | X | Phe | X |
| 83 | X | Gly | X |
| 84 | X | Ile | X |
| 85 | X | Leu | X |
| 86 | X | Met(O) | X |
| 87 | X | Arg (Pmc) | X |
| 88 | X | Ser (tBu) | X |
| 89 | X | Thr (tBu) | X |
| 90 | X | Val | X |
| 91 | X | Trp (Boc) | X |
| 92 | X | Tyr (Brz) | X |
| 93 | X | Tyr (tBu) | X |
| 94 | X | ala* | X |
| 95 | X | phe | X |
| 96 | X | ile | X |
| 97 | X | leu | X |
| 98 | X | ser | X |
| 99 | X | thr (tBu) | X |
| 100 | X | val | X |
| 101 | X | trp (Boc) | X |
| 102 | X | tyr (tBu) | X |
| 103 | X | arg (Pmc) | X |
| 104 | X | Nle | X |
| 105 | X | nle | X |
| 106 | X | Nva | X |
| 107 | X | nva | X |
| 108 | X | Nap | X |
| 109 | X | nap | X |
| 110 | X | Phg | X |
| 111 | X | Glu (tBu) | X |
| 112 | X | glu (tBu) | X |
| 113 | X | βAla | X |
| 114 | X | Cha | X |
| 115 | X | cha | X |
| 116 | X | His (Trt) | X |
| 117 | X | his (Trt) | X |
| 118 | Ala | X | X |
| 119 | Phe | X | X |
| 120 | Gly | X | X |
| 121 | Ile | X | X |
| 122 | Lys (Boc) | X | X |
| 123 | Leu | X | X |
| 124 | Met(O) | X | X |
| 125 | Asn | X | X |
| 126 | Gln | X | X |
| 127 | Arg (Pmc) | X | X |
| 128 | Ser (tBu) | X | X |
| 129 | Thr (tBu) | X | X |
| 130 | Val | X | X |
| 131 | Trp | X | X |
| 132 | Tyr | X | X |

TABLE 3-continued

LIBRARY POOL REFERENCE NUMBERS AND VARIABLE R GROUPS FOR N-BENZYL AMINOCYCLIC THIOUREA LIBRARY

| Pool No. | $R^1$ | $R^3$ | $R^4$ |
|---|---|---|---|
| 133 | Tyr (Brz) (tBu) | X | X |
| 134 | ala | X | X |
| 135 | phe | X | X |
| 136 | ile | X | X |
| 137 | lys (Boc) | X | X |
| 138 | leu | X | X |
| 139 | asn | X | X |
| 140 | gln | X | X |
| 141 | ser | X | X |
| 142 | thr (tBu) | X | X |
| 143 | val | X | X |
| 144 | trp | X | X |
| 145 | tyr (tBu) | X | X |
| 146 | arg (Pmc) | X | X |
| 147 | Nle | X | X |
| 148 | nle | X | X |
| 149 | Nva | X | X |
| 150 | nva | X | X |
| 151 | Nap | X | X |
| 152 | nap | X | X |
| 153 | Phg | X | X |
| 154 | Cha | X | X |
| 155 | cha | X | X |
| 156 | His (Trt) | X | X |
| 157 | his (Trt) | X | X |

*lower case lettering indicates D-amino acids

EXAMPLE IV

Figure 3A:
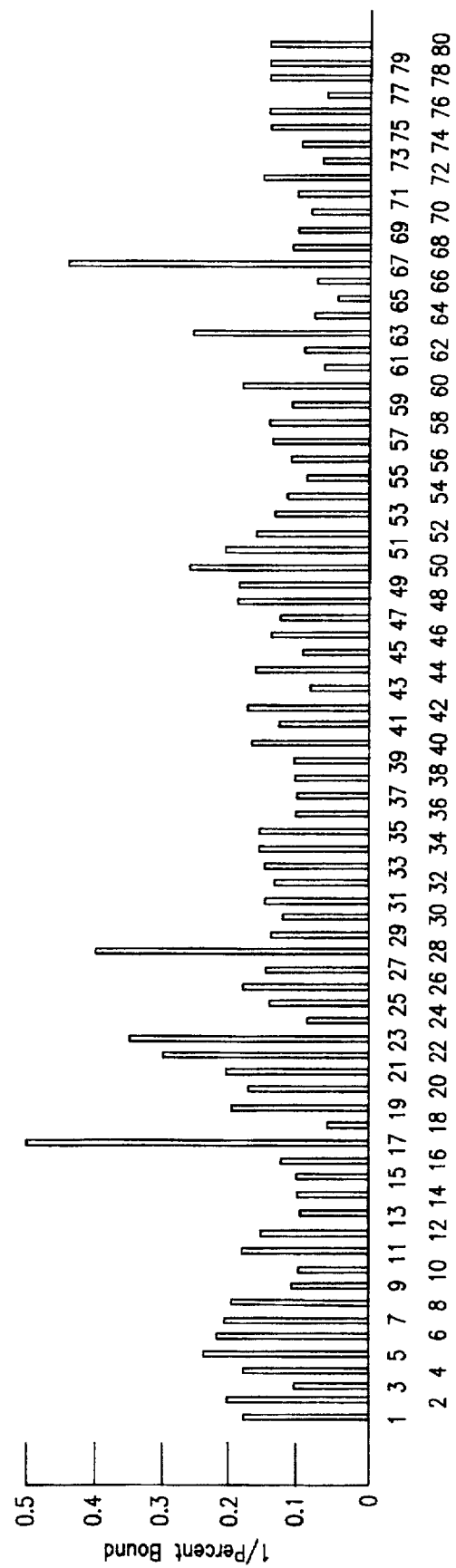
FIG. 3 graphically depicts the μ-opioid receptor screening data for the N-benzyl aminocyclic thiourea library of the subject invention (named therein as "DCR 527"). Specifically, FIG. 3a provides the μ-opioid receptor assay data for pools 1 to 80 of that library, FIG. 3b graphs the results of pools 81 to 117.
FIG. 3c depicts the data for pools 118 to 157.
Figure 3B:
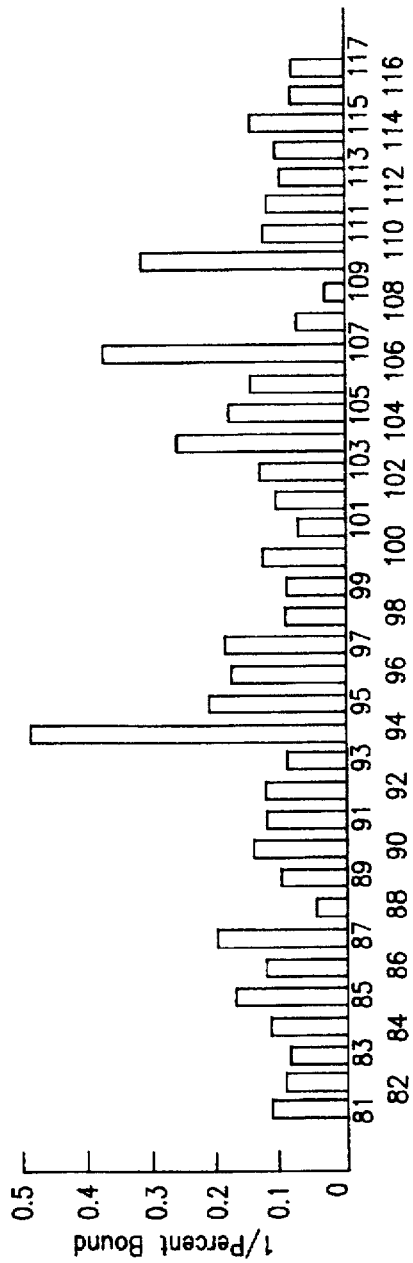
Figure 3C:
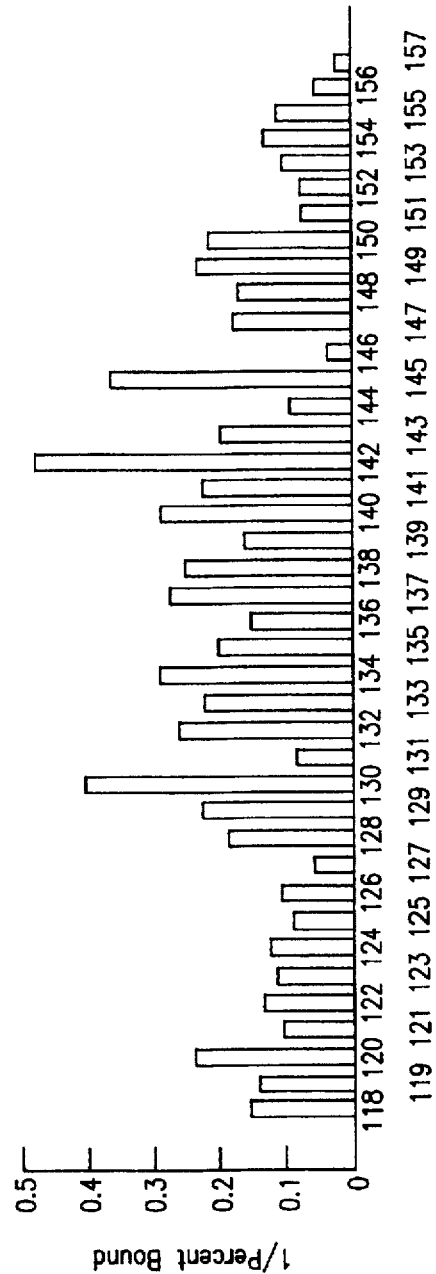
Figure 4A:
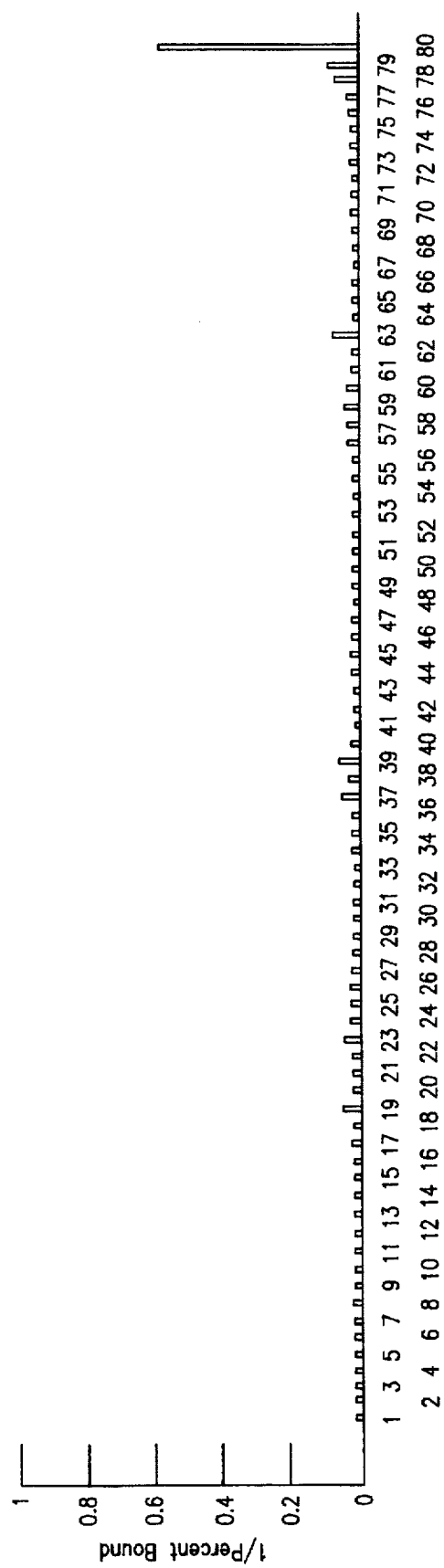
FIG. 4 provides graphs depicting the κ-opioid receptor screening data for the N-benzyl aminocyclic thiourea library (DCR 527). Specifically, FIG. 4a graphs the κ-opioid receptor assay data for pools 1 to 80 of that library, FIG. 4b provides the data for pools 81 to 117.
FIG. 4c is the data for pools 118 to 157.
Figure 4B:
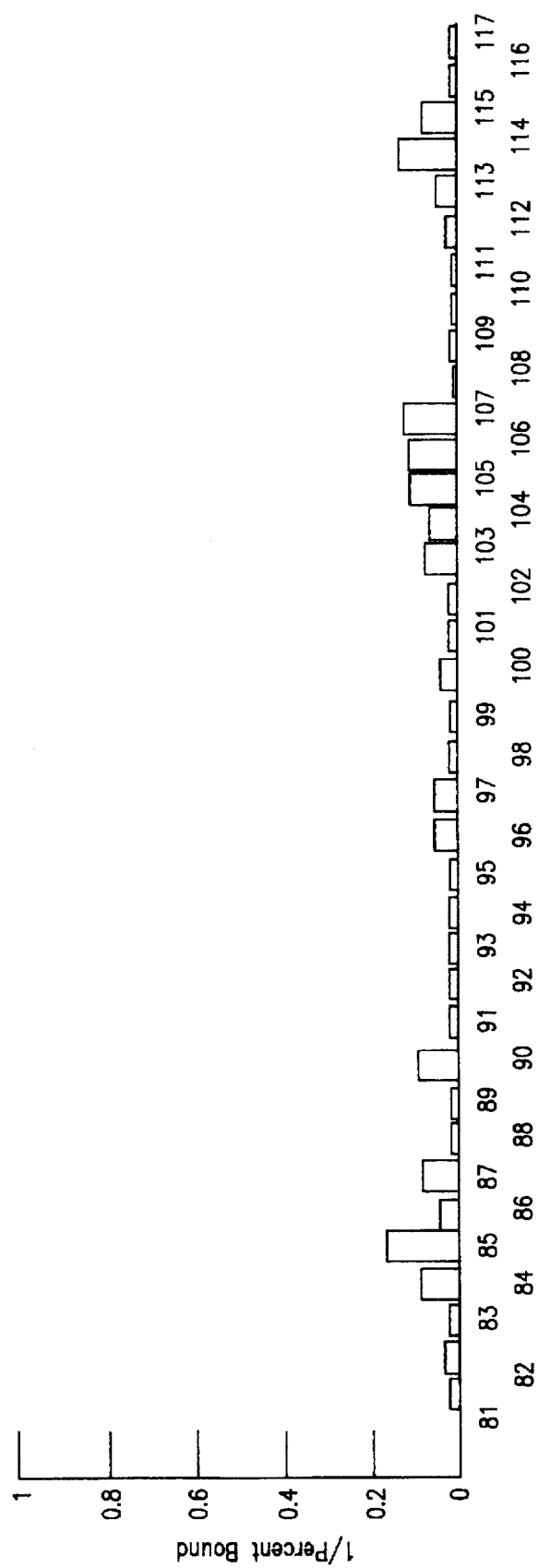
Figure 4C:
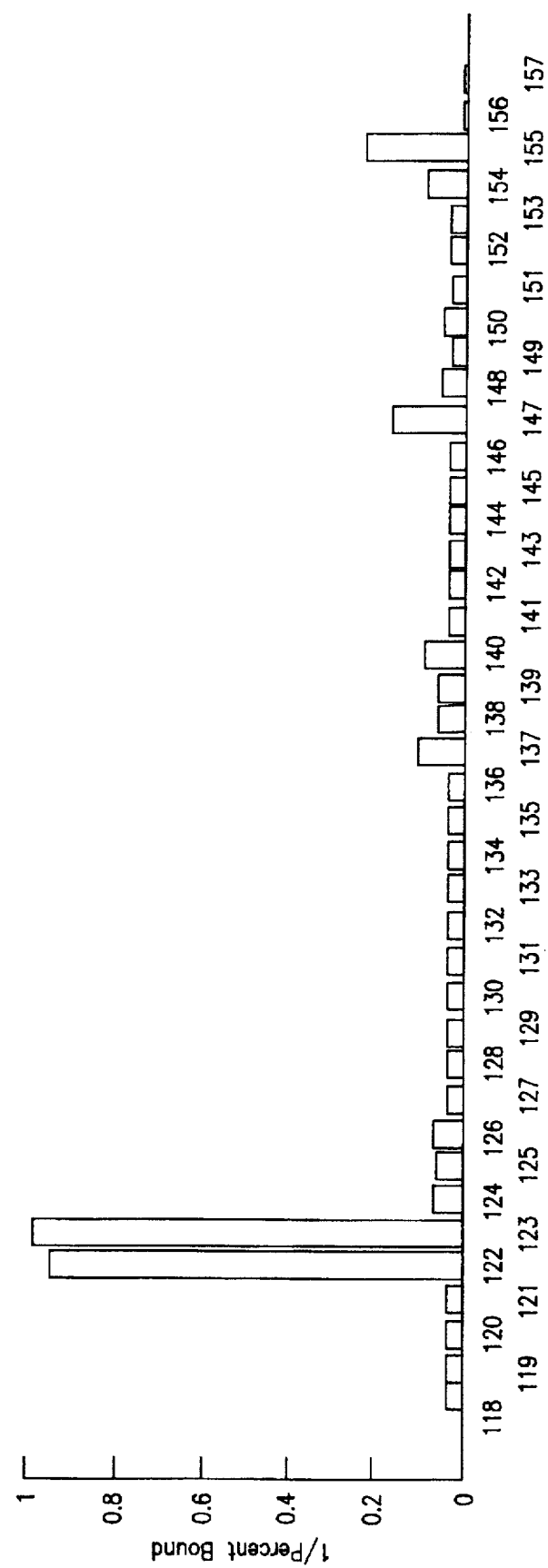

This example describes initiall biological screens of all 157 library pools as indentified in the above Example III. More specifically, this example provides an initial screens of all the N-benzyl aminocyclic thioureas in (1) the anti-microbial assay, (2) the μ-opioid receptor assay and (3) κ-opioid receptor assay, each of which are described in detail above. The results of those screens are provided in Table 4 below. In addition, the results of the μ- and κ-opioid receptor assays are depicted graphically in FIGS. 3 and 4.

The results of these assays evidence that many of the cyclic urea and thiourea compounds contained within the libraries are biologically active, either as an anti-microbial or inhibitor of a specific opioid receptor. Moreover, the results of the screens provide evidence that there is selectivity of certain compounds for one opioid receptor over another.

TABLE 4

Assays Of The N-Benzyl Aminocyclic Thiourea Library (Positional Scanning Format)

| Pool No. | Anti-Microbial Assay ($IC_{50}$, μg/ml) | μ-Opioid Receptor Assay (% Bound) | κ-Opioid Receptor Assay (% Bound) |
|---|---|---|---|
| 1 | 3.237 | 6 | 72 |
| 2 | 6.295 | 5 | 46 |
| 3 | 9.792 | 9 | 55 |
| 4 | 5.008 | 6 | 74 |
| 5 | <7.8 | 4 | 52 |
| 6 | <7.8 | 5 | 84 |
| 7 | <7.8 | 5 | 57 |
| 8 | <7.8 | 5 | 73 |
| 9 | <7.8 | 9 | 72 |
| 10 | <7.8 | 10 | 74 |
| 11 | <7.8 | 6 | 63 |
| 12 | <7.8 | 6 | 83 |
| 13 | <7.8 | 11 | 88 |
| 14 | <7.8 | 10 | 60 |
| 15 | <7.8 | 10 | 66 |
| 16 | <7.8 | 8 | 50 |
| 17 | 10.31 | 2 | 71 |
| 18 | <7.8 | 17 | 52 |
| 19 | <7.8 | 5 | 21 |
| 20 | <7.8 | 6 | 47 |
| 21 | 10.31 | 5 | 46 |
| 22 | 16.31 | 3 | 71 |
| 23 | <7.8 | 2 | 27 |
| 24 | 8.487 | 11 | 63 |
| 25 | NT | 7 | 51 |
| 26 | 8.22 | 5 | 43 |
| 27 | <7.8 | 7 | 79 |
| 28 | <7.8 | 2 | 48 |
| 29 | 15.94 | 7 | 56 |
| 30 | <7.8 | 8 | 53 |
| 31 | <7.8 | 7 | 103 |
| 32 | 21.14 | 7 | 37 |
| 33 | <7.8 | 7 | 22 |
| 34 | 10.31 | 6 | 63 |
| 35 | <7.8 | 9 | 50 |
| 36 | 7.926 | 9 | 54 |
| 37 | <7.8 | 9 | 38 |
| 38 | <7.8 | 9 | 27 |
| 39 | <7.8 | 9 | 48 |
| 40 | 10.34 | 6 | 23 |
| 41 | <7.8 | 7 | 95 |
| 42 | 10.31 | 5 | 38 |
| 43 | 12.36 | 12 | 49 |
| 44 | <7.8 | 6 | 58 |
| 45 | <7.8 | 10 | 42 |
| 46 | <7.8 | 7 | 30 |
| 47 | <7.8 | 7 | 79 |
| 48 | 18.36 | 5 | 51 |
| 49 | <7.8 | 5 | 60 |
| 50 | <7.8 | 4 | 36 |
| 51 | <7.8 | 5 | 65 |
| 52 | <7.8 | 6 | 31 |
| 53 | <7.8 | 7 | 30 |
| 54 | <7.8 | 8 | 54 |
| 55 | <7.8 | 11 | 77 |
| 56 | <7.8 | 9 | 36 |
| 57 | 10.31 | 7 | 36 |
| 58 | <7.8 | 7 | 35 |
| 59 | 9.004 | 9 | 24 |
| 60 | <7.8 | 5 | 56 |
| 61 | <7.8 | 14 | 58 |
| 62 | 8.313 | 10 | 35 |
| 63 | 10.31 | 4 | 16 |
| 64 | 8.776 | 12 | 31 |
| 65 | 9.468 | 21 | 55 |
| 66 | <7.8 | 12 | 30 |
| 67 | <7.8 | 2 | 38 |
| 68 | <7.8 | 9 | 60 |
| 69 | 13.85 | 9 | 46 |
| 70 | 17.19 | 11 | 39 |
| 71 | 8.201 | 9 | 30 |
| 72 | 7.757 | 6 | 39 |
| 73 | <7.8 | 13 | 29 |

TABLE 4-continued

Assays Of The N-Benzyl Aminocyclic Thiourea Library (Positional Scanning Format)

| Pool No. | Anti-Microbial Assay ($IC_{50}$, µg/ml) | µ-Opioid Receptor Assay (% Bound) | κ-Opioid Receptor Assay (% Bound) |
|---|---|---|---|
| 74 | <7.8 | 9 | 55 |
| 75 | 15.93 | 7 | 39 |
| 76 | NT | 7 | 76 |
| 77 | <7.8 | 14 | 59 |
| 78 | <7.8 | 7 | 25 |
| 79 | 9.985 | 7 | 17 |
| 80 | 7.54 | 7 | 2 |
| 81 | 10.5 | 9 | 43 |
| 82 | <7.8 | 11 | 35 |
| 83 | 5.274 | 12 | 62 |
| 84 | 10.31 | 9 | 11 |
| 85 | <7.8 | 6 | 6 |
| 86 | <7.8 | 8 | 21 |
| 87 | <7.8 | 5 | 11 |
| 88 | 11.02 | 20 | 66 |
| 89 | 9.603 | 9 | 65 |
| 90 | 7.719 | 7 | 9 |
| 91 | 5.895 | 8 | 67 |
| 92 | 8.052 | 8 | 47 |
| 93 | <7.8 | 10 | 53 |
| 94 | 8.441 | 2 | 37 |
| 95 | <7.8 | 5 | 38 |
| 96 | <7.8 | 5 | 21 |
| 97 | <7.8 | 5 | 19 |
| 98 | 8.925 | 9 | 52 |
| 99 | 12.45 | 10 | 63 |
| 100 | <7.8 | 7 | 27 |
| 101 | <7.8 | 12 | 108 |
| 102 | <7.8 | 8 | 53 |
| 103 | <7.8 | 7 | 11 |
| 104 | 8.241 | 4 | 16 |
| 105 | <7.8 | 5 | 9 |
| 106 | <7.8 | 6 | 8 |
| 107 | 7.837 | 3 | 7 |
| 108 | <7.8 | 11 | 54 |
| 109 | <7.8 | 25 | 69 |
| 110 | <7.8 | 3 | 26 |
| 111 | <7.8 | 7 | 84 |
| 112 | <7.8 | 8 | 59 |
| 113 | 16.34 | 9 | 29 |
| 114 | <7.8 | 8 | 7 |
| 115 | <7.8 | 7 | 12 |
| 116 | 8.097 | 11 | 68 |
| 117 | NT | 11 | 89 |
| 118 | <7.8 | 7 | 38 |
| 119 | <7.8 | 7 | 42 |
| 120 | <7.8 | 4 | 34 |
| 121 | 10.31 | 9 | 51 |
| 122 | 9.236 | 7 | 1 |
| 123 | 9.562 | 8 | 0 |
| 124 | 7.823 | 8 | 17 |
| 125 | <7.8 | 11 | 23 |
| 126 | <7.8 | 9 | 15 |
| 127 | <7.8 | 15 | 82 |
| 128 | <7.8 | 5 | 56 |
| 129 | 9.355 | 4 | 39 |
| 130 | 10.31 | 2 | 31 |
| 131 | <7.8 | 10 | 52 |
| 132 | 9.313 | 4 | 35 |
| 133 | <7.8 | 4 | 40 |
| 134 | <7.8 | 3 | 39 |
| 135 | <7.8 | 5 | 36 |
| 136 | 9.165 | 6 | 40 |
| 137 | <7.8 | 3 | 8 |
| 138 | <7.8 | 4 | 17 |
| 139 | <7.8 | 6 | 22 |
| 140 | <7.8 | 3 | 11 |
| 141 | <7.8 | 4 | 53 |
| 142 | <7.8 | 2 | 50 |
| 143 | 9.798 | 5 | 54 |
| 144 | <7.8 | 9 | 39 |
| 145 | <7.8 | 3 | 33 |
| 146 | 13.07 | 17 | 60 |
| 147 | <7.8 | 5 | 5 |
| 148 | <7.8 | 5 | 12 |
| 149 | 3.672 | 4 | 27 |
| 150 | 8.722 | 4 | 13 |
| 151 | 2.415 | 11 | 57 |
| 152 | 3.026 | 11 | 53 |
| 153 | 5.158 | 9 | 25 |
| 154 | 3.46 | 7 | 8 |
| 155 | 2.829 | 8 | 3 |
| 156 | 5.448 | 14 | 40 |
| 157 | 9.057 | 24 | 107 |

Although the invention has been described with reference to the examples provided above, it should be understood that various modifications can be made without departing from the spirit of the inventions. Accordingly the invention is limited only by the claims.

We claim:

1. A library composition of matter, comprising a combinatorial library of two or more cyclic urea compounds of the structure:

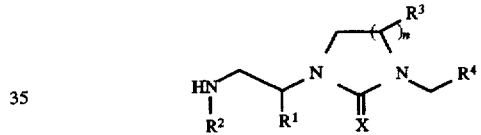

wherein:

$R^1$ is selected from the groups consisting of a hydrogen atom, $C_1$ to $C_{10}$ alkyl, $C_1$ to $C_{10}$ substituted alkyl, $C_7$ to $C_{16}$ phenylalkyl, $C_7$ to $C_{16}$ substituted phenylalkyl, phenyl, substituted phenyl, $C_3$ to $C_7$ cycloalkyl, and $C_3$ to $C_7$ substituted cycloalkyl;

$R^2$ is selected from the group consisting of $C_1$ to $C_{10}$ alkyl, $C_2$ to $C_{10}$ alkenyl, benzyl, substituted benzyl, naphthylmethyl, and substituted naphthylmethyl;

$R^3$ is selected from the group consisting of a hydrogen atom, $C_1$ to $C_{10}$ alkyl; $C_1$ to $C_{10}$ substituted alkyl, $C_7$ to $C_{16}$ phenylalkyl, $C_7$ to $C_{16}$ substituted phenylalkyl, phenyl, substituted phenyl, $C_3$ to $C_7$ cycloalkyl, and $C_3$ to $C_7$ substituted cycloalkyl;

$R^4$ is selected from the group consisting of $C_1$ to $C_{10}$ alkyl, $C_2$ to $C_{10}$ alkenyl, $C_1$ to $C_{10}$ substituted alkyl, $C_3$ to $C_7$ substituted cycloalkyl, $C_7$ to $C_{16}$ phenylalkyl, $C_7$ to $C_{16}$ substituted phenylalkyl, $C_7$ to $C_{16}$ phenylalkenyl and $C_7$ to $C_{16}$ substituted phenylalkenyl;

X is selected from the group consisting of an oxygen atom(O) and a sulfur atom(S); and n is one or two.

2. The composition of claim 1, wherein X is an oxygen atom.

3. The composition of claim 1, wherein X is a sulfur atom.

4. The composition of claim 1, wherein $R^2$ is selected from the group consisting of methyl, ethyl, benzyl, allyl, and naphthylmethyl.

5. The composition of claim 4, wherein $R^2$ is methyl.

6. The composition of claim 4, wherein $R^2$ is benzyl.

7. The composition of claim 1, wherein $R^1$ is selected from the group consisting of methyl, benzyl, hydrogen, 2-butyl, N,N-dimethylaminobutyl, N-methylaminobutyl, 2-methylpropyl, methylsulfinylethyl, N,N-dimethylaminoethyl, N,N-dimethylaminopropyl, N',N',N'-trimethylguanidinopropyl, hydroxymethyl, 1-hydroxyethyl, 2-propyl, N-methyl-3-indolylmethyl, 4-methoxybenzyl, 4-hydroxybenzyl, propyl, butyl, cyclohexylmethyl, phenyl, 2-naphthylmethyl, and 4-imidazolylmethyl;

$R^2$ is methyl;

$R^3$ is selected from the group consisting of methyl, benzyl, hydrogen, 3-hydroxypropyl, 2-butyl, N-methylaminobutyl, aminobutyl, 2-methylpropyl, methylsulfinylethyl, guanidinopropyl, hydroxymethyl, 1-hydroxyethyl, 2-propyl, N-methyl-3-indolylmethyl, 4-methoxybenzyl, 4-hydroxybenzyl, propyl, butyl, cyclohexylmethyl, phenyl, 2-naphthylmethyl, and 4-imidazolylmethyl;

$R^4$ is selected from the group consisting of 1-phenyl-1-cyclopropylmethyl, 2-phenylbutyl, 3-phenylbutyl, m-tolylethyl, 3-fluorophenethyl, 3-bromophenethyl, ($\alpha,\alpha,\alpha$-trifluoro-m-tolyl)ethyl, p-tolylethyl, 4-fluorophenethyl, 3-methoxyphenethyl, 4-bromophenethyl, 4-methoxyphenethyl, 4-ethoxyphenethyl, 4-isobutyl-$\alpha$-methylphenethyl, 3,4-dichlorophenethyl, 3,5-bis(trifluoromethyl)phenethyl, 3-(3,4-dimethoxyphenyl)propyl, 4-biphenethyl, 3-phenyl-2-methyl-2-propenyl, 3-(2-trifluoromethylphenyl)-2-propenyl, 3,4-dimethoxyphenethyl, 3,4-(dihydroxy)phenylethyl, 3-(2-methoxyphenyl)-2-propenyl, benzyl, 3-(4-chlorophenyl)-2-propenyl, trans-phenyl-2-propenyl, m-xylyl, phenethyl, 3-phenylpropyl, 4-phenylbutyl, 3,5-bis(trifluoromethyl)benzyl, butyl, heptyl, isobutyryl, (+/−)-2-methylbutyl, isovaleryl, 3-methylvaleryl, 4-methylvaleryl, 2-butenyl, 3-butenyl, p-xylyl, neopentyl, tert-butylethyl, cyclohexylmethyl, cyclohexylethyl, cyclohexylbutyl, cycloheptylmethyl, ethyl, 2-methyl-1-cyclopropylmethyl, cyclobutylmethyl, cyclopentylmethyl, 3-cyclopentylpropyl, cyclohexanepropyl, 4-methyl-1-cyclohexylmethyl, 4-tert-butyl-1-cyclohexylmethyl, 4-methylcyclohexylethyl, 2-methyl-2-butenyl, 1-adamantylethyl, 2-($\alpha,\alpha,\alpha$-trifluoro-m-toluidino)-3-pyridylmethyl, 4-nitrophenethyl, 4-(nitrophenyl)butyl, 3-(4-nitrophenyl)-2-propenyl, 2-nitrobenzyl, 2,4-dinitrophenethyl, 4-biphenethyl, 2-chloro-5-nitrobenzyl, (4-pyridylthio)ethyl, 3,3-diphenylpropyl, 2-chloro-4-nitrobenzyl, 4-dimethylaminobenzyl, 4-nitrobenzyl, 3-dimethylaminobenzyl, abietyl, 2-methyl-4-nitro-1-imidizolylpropyl, trans-styrylethyl, cyclopentylethyl, 2,2-dicyclohexylethyl, (2-pyridylthio)ethyl, pentadienyl, and 3-indolylethyl;

X is selected from the group consisting of an oxygen atom(O) and a sulfur atom(S); and n is one or two.

8. The composition of claim 7, wherein X is an oxygen atom.

9. The composition of claim 7, wherein X is a sulfur atom.

10. The composition of claim 1, wherein $R^1$ is selected from the group consisting of methyl, benzyl, hydrogen, 2-butyl, N-methyl-N-benzylaminobutyl, N-benzylaminobutyl, 2-methylpropyl, methylsulfinylethyl, N,N-dibenzylaminoethyl, N,N-dibenzylaminopropyl, guanidinopropyl, hydroxymethyl, 1-hydroxyethyl, 2-propyl, N-benzyl-3-indolylmethyl, 4-hydroxybenzyl, propyl, butyl, cyclohexylmethyl, phenyl, 2-naphthylmethyl, and 4-imidazolylmethyl;

$R^2$ is benzyl;

$R^3$ is selected from the group consisting of methyl, benzyl, hydrogen, 3-hydroxypropyl, 2-butyl, N-methylaminobutyl, aminobutyl, 2-methylpropyl, methylsulfinylethyl, guanidinopropyl, hydroxymethyl, 1-hydroxyethyl, 2-propyl, N-methyl-3-indolylmethyl, 4-methoxybenzyl, 4-hydroxybenzyl, propyl, butyl, cyclohexylmethyl, phenyl, 2-naphthylmethyl, and 4-imidazolylmethyl;

$R^4$ is selected from the group consisting of 1-phenyl-1-cyclopropylmethyl, 2-phenylbutyl, 3-phenylbutyl, m-tolylethyl, 3-fluorophenethyl, 3-bromophenethyl, ($\alpha,\alpha,\alpha$-trifluoro-m-tolyl)ethyl, p-tolylethyl, 4-fluorophenethyl, 3-methoxyphenethyl, 4-bromophenethyl, 4-methoxyphenethyl, 4-ethoxyphenethyl, 4-isobutyl-$\alpha$-methylphenethyl, 3,4-dichlorophenethyl, 3,5-bis(trifluoromethyl)phenethyl, 3-(3,4-dimethoxyphenyl)propyl, 4-biphenethyl, 3-phenyl-2-methyl-2-propenyl, 3-(2-trifluoromethylphenyl)-2-propenyl, 3,4-dimethoxyphenethyl, 3,4-(dihydroxy)phenylethyl, 3-(2-methoxyphenyl)-2-propenyl, benzyl, 3-(4-chlorophenyl)-2-propenyl, trans-phenyl-2-propenyl, m-xylyl, phenethyl, 3-phenylpropyl, 4-phenylbutyl, 3,5-bis(trifluoromethyl)benzyl, butyl, heptyl, isobutyryl, (+/−)-2-methylbutyl, isovaleryl, 3-methylvaleryl, 4-methylvaleryl, 2-butenyl, 3-butenyl, p-xylyl, neopentyl, tert-butylethyl, cyclohexylmethyl, cyclohexylethyl, cyclohexylbutyl, cycloheptylmethyl, ethyl, 2-methyl-1-cyclopropylmethyl, cyclobutylmethyl, cyclopentylmethyl, 3-cyclopentylpropyl, cyclohexanepropyl, 4-methyl-1-cyclohexylmethyl, 4-tert-butyl-1-cyclohexylmethyl, 4-methylcyclohexylethyl, 2-methyl-2-butenyl, 1-adamantylethyl, 2-($\alpha,\alpha,\alpha$-trifluoro-m-toluidino)-3-pyridylmethyl, 4-nitrophenethyl, 4-(nitrophenyl)butyl, 3-(4-nitrophenyl)-2-propenyl, 2-nitrobenzyl, 2,4-dinitrophenethyl, 4-biphenethyl, 2-chloro-5-nitrobenzyl, (4-pyridylthio)ethyl, 3,3-diphenylpropyl, 2-chloro-4-nitrobenzyl, 4-dimethylaminobenzyl, 4-nitrobenzyl, 3-dimethylaminobenzyl, abietyl, 2-methyl-4-nitro-1-imidizolylpropyl, trans-styrylethyl, cyclopentylethyl, 2,2-dicyclohexylethyl, (2-pyridylthio)ethyl, pentadienyl, and 3-indolylethyl;

X is selected from the group consisting of an oxygen atom(O) and a sulfur atom(S); and n is one or two.

11. The composition of claim 10, wherein X is an oxygen atom.

12. The composition of claim 10, wherein X is a sulfur atom.

13. A single cyclic urea compound of the structure:

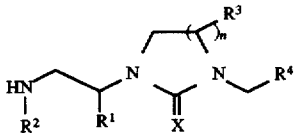

wherein:
- $R^1$ is selected from the groups consisting of a hydrogen atom, $C_1$ to $C_{10}$ alkyl, $C_1$ to $C_{10}$ substituted alkyl, $C_7$ to $C_{16}$ phenylalkyl, $C_7$ to $C_{16}$ substituted phenylalkyl, phenyl, substituted phenyl, $C_3$ to $C_7$ cycloalkyl, and $C_3$ to $C_7$ substituted cycloalkyl;
- $R^2$ is selected from the group consisting of $C_1$ to $C_{10}$ alkyl, $C_2$ to $C_{10}$ alkenyl, benzyl, substituted benzyl, naphthylmethyl, and substituted naphthylmethyl;
- $R^3$ is selected from the group consisting of a hydrogen atom, $C_1$ to $C_{10}$ alkyl, $C_1$ to $C_{10}$ substituted alkyl, $C_7$ to $C_{16}$ phenylalkyl, $C_7$ to $C_{16}$ substituted phenylalkyl, phenyl, substituted phenyl, $C_3$ to $C_7$ cycloalkyl, and $C_3$ to $C_7$ substituted cycloalkyl;
- $R^4$ is selected from the group consisting of $C_1$ to $C_{10}$ alkyl, $C_2$ to $C_{10}$ alkenyl, $C_1$ to $C_{10}$ substituted alkyl, $C_3$ to $C_7$ substituted cycloalkyl, $C_7$ to $C_{16}$ phenylalkyl, $C_7$ to $C_{16}$ substituted phenylalkyl, $C_7$ to $C_{16}$ phenylalkenyl and $C_7$ to $C_{16}$ substituted phenylalkenyl;
- X is selected from the group consisting of an oxygen atom(O) and a sulfur atom(S); and
- n is one.

14. The compound of claim 13, wherein X is an oxygen atom.

15. The compound of claim 13, wherein X is a sulfur atom.

16. The compound of claim 13, wherein $R^2$ is selected from the group consisting of methyl, ethyl, benzyl, allyl, and naphthylmethyl.

17. The compound of claim 16, wherein $R^2$ is methyl.

18. The compound of claim 16, wherein $R^2$ is benzyl.

19. The compound of claim 13, wherein $R^1$ is selected from the group consisting of methyl, benzyl, hydrogen, 2-butyl, N,N-dimethylaminobutyl, N-methylaminobutyl, 2-methylpropyl, methylsulfinylethyl, N,N-dimethylaminoethyl, N,N-dimethylaminopropyl, N',N',N'-trimethylguanidinopropyl, hydroxymethyl, 1-hydroxyethyl, 2-propyl, N-methyl-3-indolylmethyl, 4-methoxybenzyl, 4-hydroxybenzyl, propyl, butyl, cyclohexylmethyl, phenyl, 2-naphthylmethyl, and 4-imidazolylmethyl;

$R^2$ is methyl;

$R^3$ is selected from the group consisting of methyl, benzyl, hydrogen, 3-hydroxypropyl, 2-butyl, N-methylaminobutyl, aminobutyl, 2-methylpropyl, methylsulfinylethyl, guanidinopropyl, hydroxymethyl, 1-hydroxyethyl, 2-propyl, N-methyl-3-indolylmethyl, 4-methoxybenzyl, 4-hydroxybenzyl, propyl, butyl, cyclohexylmethyl, phenyl, 2-naphthylmethyl, and 4-imidazolylmethyl;

$R^4$ is selected from the group consisting of 1-phenyl-1-cyclopropylmethyl, 2-phenylbutyl, 3-phenylbutyl, m-tolylethyl, 3-fluorophenethyl, 3-bromophenethyl, (α,α,α-trifluoro-m-tolyl)ethyl, p-tolylethyl, 4-fluorophenethyl, 3-methoxyphenethyl, 4-bromophenethyl, 4-methoxyphenethyl, 4-ethoxyphenethyl, 4-isobutyl-α-methylphenethyl, 3,4-dichlorophenethyl, 3,5-bis(trifluoromethyl)phenethyl, 3-(3,4-dimethoxyphenyl)propyl, 4-biphenethyl, 3-phenyl-2-methyl-2-propenyl, 3-(2-trifluoromethylphenyl)-2-propenyl, 3,4-dimethoxyphenethyl, 3,4-(dihydroxy) phenylethyl, 3-(2-methoxyphenyl)-2-propenyl, benzyl, 3-(4-chlorophenyl)-2-propenyl, trans-phenyl-2-propenyl, m-xylyl, phenethyl, 3-phenylpropyl, 4-phenylbutyl, 3,5-bis(trifluoromethyl)benzyl, butyl, heptyl, isobutyryl, (+/−)-2-methylbutyl, isovaleryl, 3-methylvaleryl, 4-methylvaleryl, 2-butenyl, 3-butenyl, p-xylyl, neopentyl, tert-butylethyl, cyclohexylmethyl, cyclohexylethyl, cyclohexylbutyl, cycloheptylmethyl, ethyl, 2-methyl-1-cyclopropylmethyl, cyclobutylmethyl, cyclopentylmethyl, 3-cyclopentylpropyl, cyclohexanepropyl, 4-methyl-1-cyclohexylmethyl, 4-tert-butyl-1-cyclohexylmethyl, 4-methylcyclohexylethyl, 2-methyl-2-butenyl, 1-adamantylethyl, 2-(α, α,α-trifluoro-m-toluidino)-3-pyridylmethyl, 4-nitrophenethyl, 4-(nitrophenyl)butyl, 3-(4-nitrophenyl)-2-propenyl, 2-nitrobenzyl, 2,4-dinitrophenethyl, 4-biphenethyl, 2-chloro-5-nitrobenzyl, (4-pyridylthio)ethyl, 3,3-diphenylpropyl, 2-chloro-4-nitrobenzyl, 4-dimethylaminobenzyl, 4-nitrobenzyl, 3-dimethylaminobenzyl, abietyl, 2-methyl-4-nitro-1-imidizolylpropyl, trans-styrylethyl, cyclopentylethyl, 2,2-dicyclohexylethyl, (2-pyridylthio)ethyl, pentadienyl, and 3-indolylethyl;

X is selected from the group consisting of an oxygen atom(O) and a sulfur atom(S); and n is one.

20. The compound of claim 19, wherein X is an oxygen atom.

21. The compound of claim 19, wherein X is a sulfur atom.

22. The compound of claim 13, wherein $R^1$ is selected from the group consisting of methyl, benzyl, hydrogen, 2-butyl, N-methyl-N-benzylaminobutyl, N-benzylaminobutyl, 2-methylpropyl, methylsulfinylethyl, N,N-dibenzylaminoethyl, N,N-dibenzylaminopropyl, guanidinopropyl, hydroxymethyl, 1-hydroxyethyl, 2-propyl, N-benzyl-3-indolylmethyl, 4-hydroxybenzyl, propyl, butyl, cyclohexylmethyl, phenyl, 2-naphthylmethyl, and 4-imidazolylmethyl;

$R^2$ is benzyl;

$R^3$ is selected from the group consisting of methyl, benzyl, hydrogen, 3-hydroxypropyl, 2-butyl, N-methylaminobutyl, aminobutyl, 2-methylpropyl, methylsulfinylethyl, guanidinopropyl, hydroxymethyl, 1-hydroxyethyl, 2-propyl, N-methyl-3-indolylmethyl, 4-methoxybenzyl, 4-hydroxybenzyl, propyl, butyl, cyclohexylmethyl, phenyl, 2-naphthylmethyl, and 4-imidazolylmethyl;

$R^4$ is selected from the group consisting of 1-phenyl-1-cyclopropylmethyl, 2-phenylbutyl, 3-phenylbutyl, m-tolylethyl, 3-fluorophenethyl, 3-bromophenethyl, (α,α,α-trifluoro-m-tolyl)ethyl, p-tolylethyl, 4-fluorophenethyl, 3-methoxyphenethyl, 4-bromophenethyl, 4-methoxyphenethyl, 4-ethoxyphenethyl, 4-isobutyl-α-methylphenethyl, 3,4-dichlorophenethyl, 3,5-bis(trifluoromethyl)phenethyl, 3-(3,4-dimethoxyphenyl)propyl, 4-biphenethyl, 3-phenyl-2-methyl-2-propenyl, 3-(2- trifluoromethylphenyl)-2-propenyl, 3,4-dimethoxyphenethyl, 3,4-(dihydroxy)phenylethyl, 3-(2-methoxyphenyl)-2-propenyl, benzyl, 3-(4-chlorophenyl)-2-propenyl, trans-phenyl-2-propenyl, m-xylyl, phenethyl, 3-phenylpropyl, 4-phenylbutyl, 3,5-bis(trifluoromethyl)benzyl, butyl, heptyl, isobutyryl, (+/−)-2-methylbutyl, isovaleryl, 3-methylvaleryl, 4-methylvaleryl, 2-butenyl, 3-butenyl, p-xylyl, neopentyl, tert-butylethyl, cyclohexylmethyl, cyclohexylethyl, cyclohexylbutyl, cycloheptylmethyl, ethyl, 2-methyl-1-cyclopropylmethyl, cyclobutylmethyl, cyclopentylmethyl, 3-cyclopentylpropyl, cyclohexanepropyl, 4-methyl-1-cyclohexylmethyl, 4-tert-butyl-1-cyclohexylmethyl, 4-methylcyclohexylethyl, 2-methyl-2-butenyl, 1-adamantylethyl, 2-(α,α,α-trifluoro-m-toluidino)-3-pyridylmethyl, 4-nitrophenethyl, 4-(nitrophenyl)butyl, 3-(4-nitrophenyl)-2-propenyl, 2-nitrobenzyl, 2,4-dinitrophenethyl, 4-biphenethyl, 2-chloro-5-nitrobenzyl, (4-pyridylthio)ethyl, 3,3-diphenylpropyl, 2-chloro-4-nitrobenzyl, 4-dimethylaminobenzyl, 4-nitrobenzyl, 3-dimethylaminobenzyl, abietyl, 2-methyl-4-nitro-1-imidizolylpropyl, trans-styrylethyl, cyclopentylethyl, 2,2-dicyclohexylethyl, (2-pyridylthio)ethyl, pentadienyl, and 3-indolylethyl;

X is an oxygen atom(O) or a sulfur atom(S); and n is one.

23. The compound of claim 22, wherein X is an oxygen atom.

24. The compound of claim 22, wherein X is a sulfur atom.

25. A single cyclic urea compound of the structure:

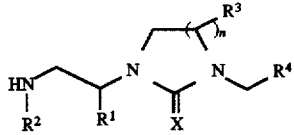

wherein:

R$^1$ is selected from the groups consisting of a hydrogen atom, C$_1$ to C$_{10}$ alkyl, C$_1$ to C$_{10}$ substituted alkyl, C$_7$ to C$_{16}$ phenyialkyl, C$_7$ to C$_{16}$ substituted phenylalkyl, phenyl, substituted phenyl, C$_3$ to C$_7$ cycloalkyl, and C$_3$ to C$_7$ substituted cycloalkyl;

R$^2$ is selected from the group consisting of C$_1$ to C$_{10}$ alkyl, C$_2$ to C$_{10}$ alkenyl, benzyl, substituted benzyl, naphthylmethyl, and substituted naphthylmethyl;

R$^3$ is selected from the group consisting of C$_1$ to C$_{10}$ alkyl; C$_1$ to C$_{10}$ substituted alkyl, C$_7$ to C$_{16}$ phenylalkyl, C$_7$ to C$_{16}$ substituted phenylalkyl, phenyl, substituted phenyl, C$_3$ to C$_7$ cycloalkyl, and C$_3$ to C$_7$ substituted cycloalkyl;

R$^4$ is selected from the group consisting of C$_1$ to C$_{10}$ alkyl, C$_2$ to C$_{10}$ alkenyl, C$_1$ to C$_{10}$ substituted alkyl, C$_3$ to C$_7$ substituted cycloalkyl, C$_7$ to C$_{16}$ phenylalkyl, C$_7$ to C$_{16}$ substituted phenylalkyl, C$_7$ to C$_{16}$ phenylalkenyl and C$_7$ to C$_{16}$ substituted phenylalkenyl;

X is selected from the group consisting of an oxygen atom(O) and a sulfur atom(S); and n is one or two.

26. The compound of claim 25, wherein X is an oxygen atom.

27. The compound of claim 25, wherein X is a sulfur atom.

28. The compound of claim 25, wherein R$^2$ is selected from the group consisting of methyl, ethyl, benzyl, allyl, and naphthylmethyl.

29. The compound of claim 28, wherein R$^2$ is methyl.

30. The compound of claim 28, wherein R$^2$ is benzyl.

31. The compound of claim 25, wherein

R$^1$ is selected from the group consisting of methyl, benzyl, hydrogen, 2-butyl, N,N-dimethylaminobutyl, N-methylaminobutyl, 2-methylpropyl, methylsulfinylethyl, N,N-dimethylaminoethyl, N,N-dimethylaminopropyl, N',N',N'-trimethylguanidinopropyl, hydroxymethyl, 1-hydroxyethyl, 2-propyl, N-methyl-3-indolylmethyl, 4-methoxybenzyl, 4-hydroxybenzyl, propyl, butyl, cyclohexylmethyl, phenyl, 2-naphthylmethyl, and 4-imidazolylmethyl;

R$^2$ is methyl;

R$^3$ is selected from the group consisting of methyl, benzyl, hydrogen, 3-hydroxypropyl, 2-butyl, N-methylaminobutyl, aminobutyl, 2-methylpropyl, methylsulfinylethyl, guanidinopropyl, hydroxymethyl, 1-hydroxyethyl, 2-propyl, N-methyl-3-indolylmethyl, 4-methoxybenzyl, 4-hydroxybenzyl, propyl, butyl, cyclohexylmethyl, phenyl, 2-naphthylmethyl, and 4-imidazolylmethyl;

R$^4$ is selected from the group consisting of 1-phenyl-1-cyclopropylmethyl, 2-phenylbutyl, 3-phenylbutyl, m-tolylethyl, 3-fluorophenethyl, 3-bromophenethyl, (α,α,α-trifluoro-m-tolyl)ethyl, p-tolylethyl, 4-fluorophenethyl, 3-methoxyphenethyl, 4-bromophenethyl, 4-methoxyphenethyl, 4-ethoxyphenethyl, 4-isobutyl-α-methylphenethyl, 3,4-dichlorophenethyl, 3,5-bis(trifluoromethyl) phenethyl, 3-(3,4-dimethoxyphenyl)propyl, 4-biphenethyl, 3-phenyl-2-methyl-2-propenyl, 3-(2-trifluoromethylphenyl)-2-propenyl, 3,4-dimethoxyphenethyl, 3,4-(dihydroxy)phenylethyl, 3-(2-methoxyphenyl)-2-propenyl, benzyl, 3-(4-chlorophenyl)-2-propenyl, trans-phenyl-2-propenyl, m-xylyl, phenethyl, 3-phenylpropyl, 4-phenylbutyl, 3,5-bis(trifluoromethyl)benzyl, butyl, heptyl, isobutyryl, (+/−)-2-methylbutyl, isovaleryl, 3-methylvaleryl, 4-methylvaleryl, 2-butenyl, 3-butenyl, p-xylyl, neopentyl, tert-butylethyl, cyclohexylmethyl, cyclohexylethyl, cyclohexylbutyl, cycloheptylmethyl, ethyl, 2-methyl-1-cyclopropylmethyl, cyclobutylmethyl, cyclopentylmethyl, 3-cyclopentylpropyl, cyclohexanepropyl, 4-methyl-1-cyclohexylmethyl, 4-tert-butyl-1-cyclohexylmethyl, 4-methylcyclohexylethyl, 2-methyl-2-butenyl, 1-adamantylethyl, 2-(α,α,α-trifluoro-m-toluidino)-3-pyridylmethyl, 4-nitrophenethyl, 4-(nitrophenyl)butyl, 3-(4-nitrophenyl)-2-propenyl, 2-nitrobenzyl, 2,4-dinitrophenethyl, 4-biphenethyl, 2-chloro-5-nitrobenzyl, (4-pyridylthio)ethyl, 3,3-diphenylpropyl, 2-chloro-4-nitrobenzyl, 4-dimethylaminobenzyl, 4-nitrobenzyl, 3-dimethylaminobenzyl, abietyl, 2-methyl-4-nitro-1-imidizolylpropyl, trans-styrylethyl, cyclopentylethyl, 2,2-dicyclohexylethyl, (2-pyridylthio)ethyl, pentadienyl, and 3-indolylethyl;

X is selected from the group consisting of an oxygen atom(O) and a sulfur atom(S); and n is one or two.

32. The compound of claim 31, wherein X is an oxygen atom.

33. The compound of claim 31, wherein X is a sulfur atom.

34. The compound of claim 25, wherein

R³ is selected from the group consisting of methyl, benzyl, hydrogen, 2-butyl, N-methyl-N-benzylaminobutyl, N-benzylaminobutyl, 2-methylpropyl, methylsulfinylethyl, N,N-dibenzylaminoethyl, N,N-dibenzylaminopropyl, guanidinopropyl, hydroxymethyl, 1-hydroxyethyl, 2-propyl, N-benzyl-3-indolylmethyl, 4-hydroxybenzyl, propyl, butyl, cyclohexylmethyl, phenyl, 2-naphthylmethyl, and 4-imidazolylmethyl;

R² is benzyl;

R³ is selected from the group consisting of methyl, benzyl, hydrogen, 3-hydroxypropyl, 2-butyl, N-methylaminobutyl, aminobutyl, 2-methylpropyl, methylsulfinylethyl, guanidinopropyl, hydroxymethyl, 1-hydroxyethyl, 2-propyl, N-methyl-3-indolylmethyl, 4-methoxybenzyl, 4-hydroxybenzyl, propyl, butyl, cyclohexylmethyl, phenyl, 2-naphthylmethyl, and 4-imidazolylmethyl;

R⁴ is selected from the group consisting of 1-phenyl-1-cyclopropylmethyl, 2-phenylbutyl, 3-phenylbutyl, m-tolylethyl, 3-fluorophenethyl, 3-bromophenethyl, (α,α,α-trifluoro-m-tolyl)ethyl, p-tolylethyl, 4-fluorophenethyl, 3-methoxyphenethyl, 4-bromophenethyl, 4-methoxyphenethyl, 4-ethoxyphenethyl, 4-isobutyl-α-methylphenethyl, 3,4-dichlorophenethyl, 3,5-bis(trifluoromethyl)phenethyl, 3-(3,4-dimethoxyphenyl)propyl, 4-biphenethyl, 3-phenyl-2-methyl-2-propenyl, 3-(2-trifluoromethylphenyl)-2-propenyl, 3,4-dimethoxyphenethyl, 3,4-(dihydroxy)phenylethyl, 3-(2-methoxyphenyl)-2-propenyl, benzyl, 3-(4-chlorophenyl)-2-propenyl, trans-phenyl-2-propenyl, m-xylyl, phenethyl, 3-phenylpropyl, 4-phenylbutyl, 3,5-bis(trifluoromethyl)benzyl, butyl, heptyl, isobutyryl, (+/−)-2-methylbutyl, isovaleryl, 3-methylvaleryl, 4-methylvaleryl, 2-butenyl, 3-butenyl, p-xylyl, neopentyl, tert-butylethyl, cyclohexylmethyl, cyclohexylethyl, cyclohexylbutyl, cycloheptylmethyl, ethyl, 2-methyl-1-cyclopropylmethyl, cyclobutylmethyl, cyclopentylmethyl, 3-cyclopentylpropyl, cyclohexanepropyl, 4-methyl-1-cyclohexylmethyl, 4-tert-butyl-1-cyclohexylmethyl, 4-methylcyclohexylethyl, 2-methyl-2-butenyl, 1-adamantylethyl, 2-(α,α,α-trifluoro-m-toluidino)-3-pyridylmethyl, 4-nitrophenethyl, 4-(nitrophenyl)butyl, 3-(4-nitrophenyl)-2-propenyl, 2-nitrobenzyl, 2,4-dinitrophenethyl, 4-biphenethyl, 2-chloro-5-nitrobenzyl, (4-pyridylthio)ethyl, 3,3-diphenylpropyl, 2-chloro-4-nitrobenzyl, 4-dimethylaminobenzyl, 4-nitrobenzyl, 3-dimethylaminobenzyl, abietyl, 2-methyl-4-nitro-1-imidizolylpropyl, trans-styrylethyl, cyclopentylethyl, 2,2-dicyclohexylethyl, (2-pyridylthio)ethyl, pentadienyl, and 3-indolylethyl;

X is an oxygen atom(O) or a sulfur atom(S); and n is one or two.

35. The compound of claim 34, wherein X is an oxygen atom.

36. The compound of claim 34, wherein X is a sulfur atom.

37. A single cyclic urea compound of the structure:

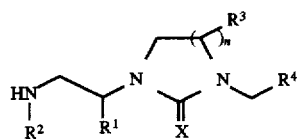

wherein:

R¹ is selected from the groups consisting of a hydrogen atom, $C_1$ to $C_{10}$ alkyl, $C_1$ to $C_{10}$ substituted alkyl, $C_7$ to $C_{16}$ phenylalkyl, $C_7$ to $C_{16}$ substituted phenylalkyl, phenyl, substituted phenyl, $C_3$ to $C_7$ cycloalkyl, and $C_3$ to $C_7$ substituted cycloalkyl;

R² is selected from the group consisting of $C_1$ to $C_{10}$ alkyl, $C_2$ to $C_{10}$ alkenyl, benzyl, substituted benzyl, naphthylmethyl, and substituted naphthylmethyl;

R³ is selected from the group consisting of a hydrogen atom, $C_1$ to $C_{10}$ alkyl, $C_1$ to $C_{10}$ substituted alkyl, $C_7$ to $C_{16}$ phenylalkyl, $C_7$ to $C_{16}$ substituted phenylalkyl, phenyl, substituted phenyl, $C_3$ to $C_7$ cycloalkyl, and $C_3$ to $C_7$ substituted cycloalkyl;

R⁴ is selected from the group consisting of 1-phenyl-1-cyclopropylmethyl, 2-phenylbutyl, 3-phenylbutyl, m-tolylethyl, 3-fluorophenethyl, 3-bromophenethyl, (α,α,α-trifluoro-m-tolyl)ethyl, p-tolylethyl, 4-fluorophenethyl, 3-methoxyphenethyl, 4-bromophenethyl, 4-methoxyphenethyl, 4-ethoxyphenethyl, 4-isobutyl-α-methylphenethyl, 3,4-dichlorophenethyl, 3,5-bis(trifluoromethyl)phenethyl, 3-(3,4-dimethoxyphenyl)propyl, 4-biphenethyl, 3-phenyl-2-methyl-2-propenyl, 3-(2-trifluoromethylphenyl)-2-propenyl, 3,4-dimethoxyphenethyl, 3,4-(dihydroxy)phenylethyl, 3-(2-methoxyphenyl)-2-propenyl, benzyl, 3-(4-chlorophenyl)-2-propenyl, trans-phenyl-2-propenyl, m-xylyl, phenethyl, 3-phenylpropyl, 4-phenylbutyl, 3,5-bis(trifluoromethyl)benzyl, butyl, heptyl, isobutyryl, (+/−)-2-methylbutyl, isovaleryl, 3-methylvaleryl, 4-methylvaleryl, 2-butenyl, 3-butenyl, p-xylyl, neopentyl, tert-butylethyl, cyclohexylmethyl, cyclohexylethyl, cyclohexylbutyl, cycloheptylmethyl, ethyl, 2-methyl-1-cyclopropylmethyl, cyclobutylmethyl, cyclopentylmethyl, 3-cyclopentylpropyl, cyclohexanepropyl, 4-methyl-1-cyclohexylmethyl, 4-tert-butyl-1-cyclohexylmethyl, 4-methylcyclohexylethyl, 2-methyl-2-butenyl, 1-adamantylethyl, 2-(α,α,α-trifluoro-m-toluidino)-3-pyridylmethyl, 4-nitrophenethyl, 4-(nitrophenyl)butyl, 3-(4-nitrophenyl)-2-propenyl, 2-nitrobenzyl, 2,4-dinitrophenethyl, 4-biphenethyl, 2-chloro-5-nitrobenzyl, (4-pyridylthio)ethyl, 3,3-diphenylpropyl, 2-chloro-4-nitrobenzyl, 4-dimethylaminobenzyl, 4-nitrobenzyl, 3-dimethylaminobenzyl, abietyl, 2-methyl-4-nitro-1-imidizolylpropyl, trans-styrylethyl, cyclopentylethyl, 2,2-dicyclohexylethyl, (2-pyridylthio)ethyl, pentadienyl, and 3-indolylethyl;

X is selected from the group consisting of an oxygen atom(O) and a sulfur atom(S); and n is one or two.

38. The compound of claim 37, wherein X is an oxygen atom.

39. The compound of claim 37, wherein X is a sulfur atom.

40. The compound of claim 37, wherein R² is selected from the group consisting of methyl, ethyl, benzyl, allyl, and naphthylmethyl.

41. The compound of claim 40, wherein $R^2$ is methyl.

42. The compound of claim 40, wherein $R^2$ is benzyl.

43. The compound of claim 37, wherein $R^1$ is selected from the group consisting of methyl, benzyl, hydrogen, 2-butyl, N,N-dimethylaminobutyl, N-methylaminobutyl, 2-methylpropyl, methylsulfinylethyl, N,N-dimethylaminoethyl, N,N-dimethylaminopropyl, N',N',N'-trimethylguanidinopropyl, hydroxymethyl, 1-hydroxyethyl, 2-propyl, N-methyl-3-indolylmethyl, 4-methoxybenzyl, 4-hydroxybenzyl, propyl, butyl, cyclohexylmethyl, phenyl, 2-naphthylmethyl, and 4-imidazolylmethyl;

$R^2$ is methyl;

$R^3$ is selected from the group consisting of methyl, benzyl, hydrogen, 3-hydroxypropyl, 2-butyl, N-methylaminobutyl, aminobutyl, 2-methylpropyl, methylsulfinylethyl, guanidinopropyl, hydroxymethyl, 1-hydroxyethyl, 2-propyl, N-methyl-3-indolylmethyl, 4-methoxybenzyl, 4-hydroxybenzyl, propyl, butyl, cyclohexylmethyl, phenyl, 2-naphthylmethyl, and 4-imidazolylmethyl;

X is selected from the group consisting of an oxygen atom(O) and a sulfur atom(s); and n is one or two.

44. The compound of claim 43, wherein X is an oxygen atom.

45. The compound of claim 43, wherein X is a sulfur atom.

46. The compound of claim 37, wherein $R^1$ is selected from the group consisting of methyl, benzyl, hydrogen, 2-butyl, N-methyl-N-benzylaminobutyl, N-benzylaminobutyl, 2-methylpropyl, methylsulfinylethyl, N,N-dibenzylaminoethyl, N,N-dibenzylaminopropyl, guanidinopropyl, hydroxymethyl, 1-hydroxyethyl, 2-propyl, N-benzyl-3-indolylmethyl, 4-hydroxybenzyl, propyl, butyl, cyclohexylmethyl, phenyl, 2-naphthylmethyl, and 4-imidazolylmethyl;

$R^2$ is benzyl;

$R^3$ is selected from the group consisting of methyl, benzyl, hydrogen, 3-hydroxypropyl, 2-butyl, N-methylaminobutyl, aminobutyl, 2-methylpropyl, methylsulfinylethyl, guanidinopropyl, hydroxymethyl, 1-hydroxyethyl, 2-propyl, N-methyl-3-indolylmethyl, 4-methoxybenzyl, 4-hydroxybenzyl, propyl, butyl, cyclohexylmethyl, phenyl, 2-naphthylmethyl, and 4-imidazolylmethyl;

X is an oxygen atom(O) or a sulfur atom(S); and n is one or two.

47. The compound of claim 46, wherein X is an oxygen atom.

48. The compound of claim 46, wherein X is a sulfur atom.

49. A single cyclic urea compound of the structure:

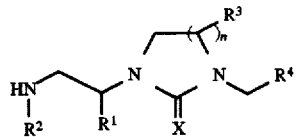

wherein:

$R^1$ is selected from the groups consisting of a hydrogen atom, $C_1$ to $C_{10}$ alkyl; $C_1$ to $C_{10}$ substituted alkyl, $C_7$ to $C_{16}$ phenylalkyl, $C_7$ to $C_{16}$ substituted phenylalkyl, phenyl, substituted phenyl, $C_3$ to $C_7$ cycloalkyl, and $C_3$ to $C_7$ substituted cycloalkyl;

$R^2$ is benzyl;

$R^3$ is selected from the group consisting of a hydrogen atom, $C_1$ to $C_{10}$ alkyl, $C_1$ to $C_{10}$ substituted alkyl, $C_7$ to $C_{16}$ phenylalkyl, $C_7$ to $C_{16}$ substituted phenylalkyl, phenyl, substituted phenyl, $C_3$ to $C_7$ cycloalkyl, and $C_3$ to $C_7$ substituted cycloalkyl;

$R^4$ is selected from the group consisting of $C_1$ to $C_{10}$ alkyl, $C_2$ to $C_{10}$ alkenyl, $C_1$ to $C_{10}$ substituted alkyl, $C_3$ to $C_7$ substituted cycloalkyl, $C_7$ to $C_{16}$ phenylalkyl, $C_7$ to $C_{16}$ substituted phenylalkyl; $C_7$ to $C_{16}$ phenylalkenyl and $C_7$ to $C_{16}$ substituted phenylalkenyl;

X is selected from the group consisting of an oxygen atom(O) and a sulfur atom(S); and n is one or two.

* * * * *